United States Patent
Kaneda et al.

(10) Patent No.: US 8,130,281 B2
(45) Date of Patent: Mar. 6, 2012

(54) INFORMATION PROCESSING APPARATUS, EYE OPEN/CLOSED DEGREE DETERMINATION METHOD, COMPUTER-READABLE STORAGE MEDIUM, AND IMAGE SENSING APPARATUS

(75) Inventors: Yuji Kaneda, Kawasaki (JP); Masakazu Matsugu, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 389 days.

(21) Appl. No.: 12/392,917

(22) Filed: Feb. 25, 2009

(65) Prior Publication Data

US 2009/0219405 A1    Sep. 3, 2009

(30) Foreign Application Priority Data

Feb. 29, 2008  (JP) ................. 2008-051121

(51) Int. Cl.
*H04N 5/228* (2006.01)
(52) U.S. Cl. .................. 348/222.1; 340/575; 340/576; 340/573.1
(58) Field of Classification Search ............... 348/222.1; 382/117, 118, 291, 104; 340/575, 576, 573.1
See application file for complete search history.

(56) References Cited

U.S. PATENT DOCUMENTS

| | | | |
|---|---|---|---|
| 5,878,156 A | 3/1999 | Okumura | |
| 7,039,233 B2 | 5/2006 | Mori et al. | |
| 7,054,850 B2 | 5/2006 | Matsugu | |
| 7,274,819 B2 | 9/2007 | Matsugu | |
| 2006/0074653 A1 | 4/2006 | Mitari et al. | |
| 2006/0115157 A1* | 6/2006 | Mori et al. | 382/190 |
| 2006/0204053 A1 | 9/2006 | Mori et al. | |
| 2006/0228005 A1 | 10/2006 | Matsugu et al. | |
| 2007/0242856 A1 | 10/2007 | Suzuki et al. | |
| 2008/0219516 A1 | 9/2008 | Suzuki et al. | |
| 2009/0089235 A1 | 4/2009 | Torii et al. | |

FOREIGN PATENT DOCUMENTS

| | | |
|---|---|---|
| JP | 9-044685 A | 2/1997 |
| JP | 11-242744 A | 9/1999 |
| JP | 2004-192551 A | 7/2004 |
| JP | 2007-241937 A | 9/2007 |

OTHER PUBLICATIONS

U.S. Appl. No. 12/392,917, filed Feb. 25, 2009: Applicants: Kaneda et al.

U.S. Appl. No. 12/485,020, filed Jun. 15, 2009: Applicants: Kaneda et al.

* cited by examiner

*Primary Examiner* — Yogesh Aggarwal

(74) *Attorney, Agent, or Firm* — Fitzpatrick, Cella, Harper & Scinto

(57) ABSTRACT

An information processing apparatus inputs an image, detects the face of a person from the input image, and calculates a feature amount associated with the open/closed state of eyes of the detected face. In addition, the information processing apparatus calculates, as a feature-change amount, the difference between the calculated feature amount and a predetermined feature amount, and calculates the eye open/closed degree of eyes of the detected face on the basis of the feature amount and the feature-change amount.

13 Claims, 22 Drawing Sheets

FIG. 9
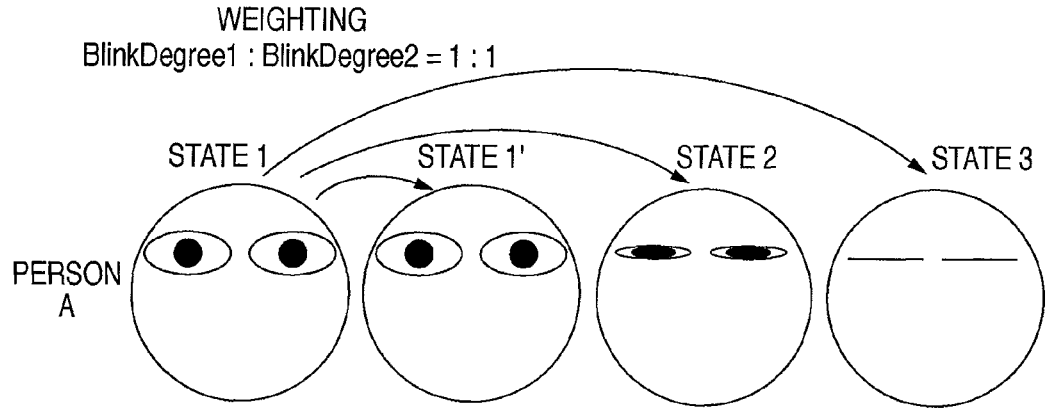
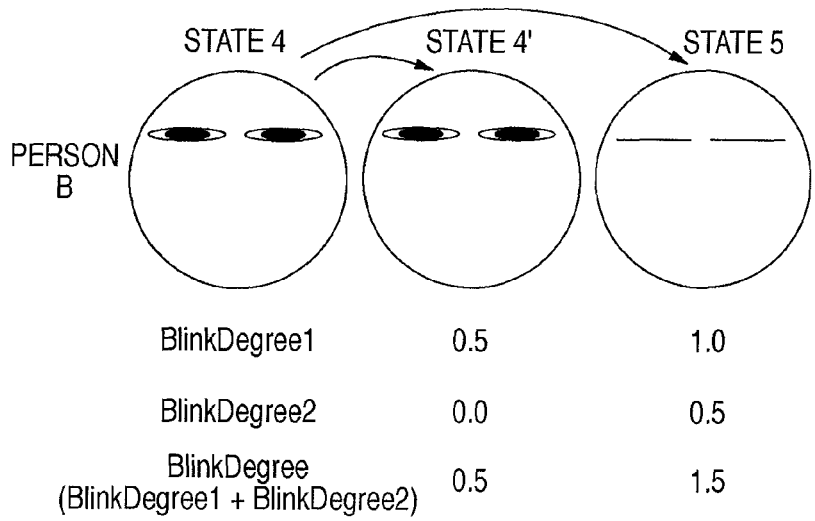

FIG. 13
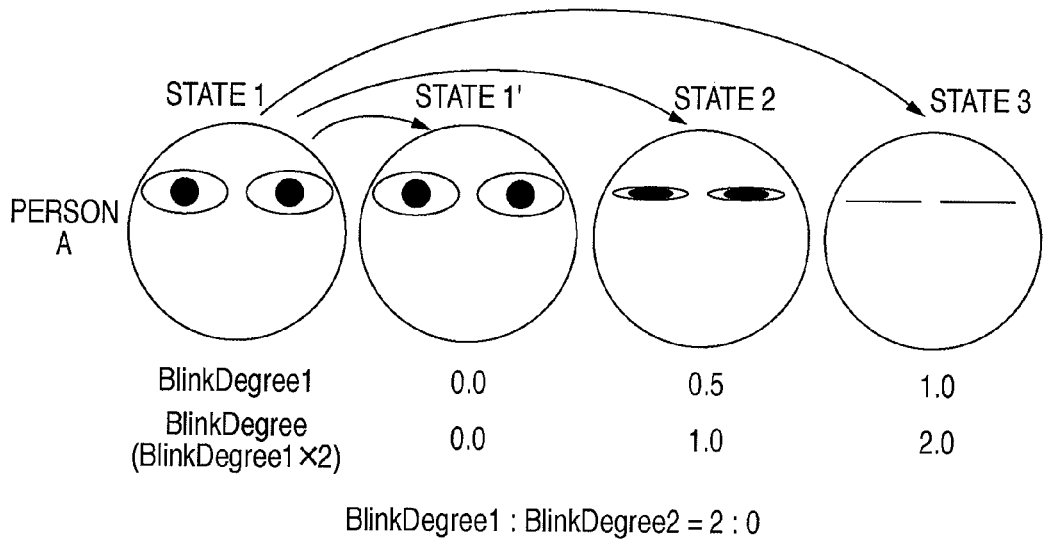
BlinkDegree1 : BlinkDegree2 = 2 : 0
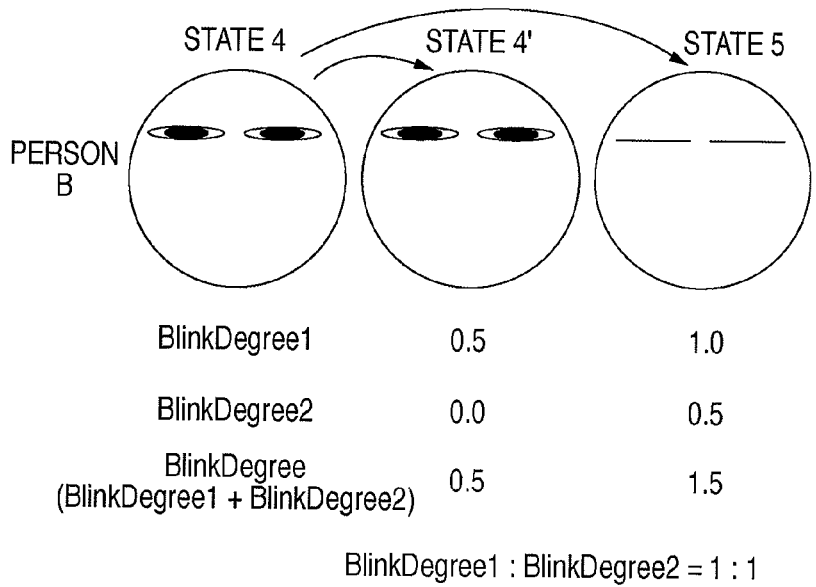
BlinkDegree1 : BlinkDegree2 = 1 : 1

FIG. 17
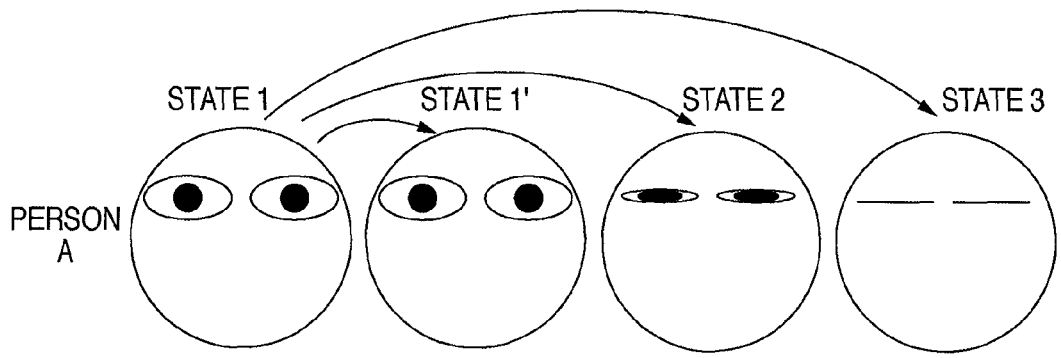
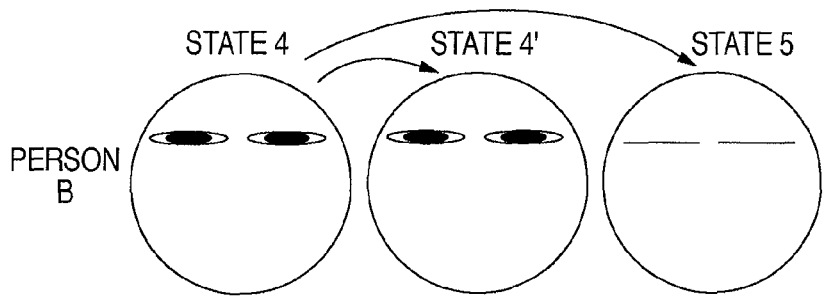

FIG. 18
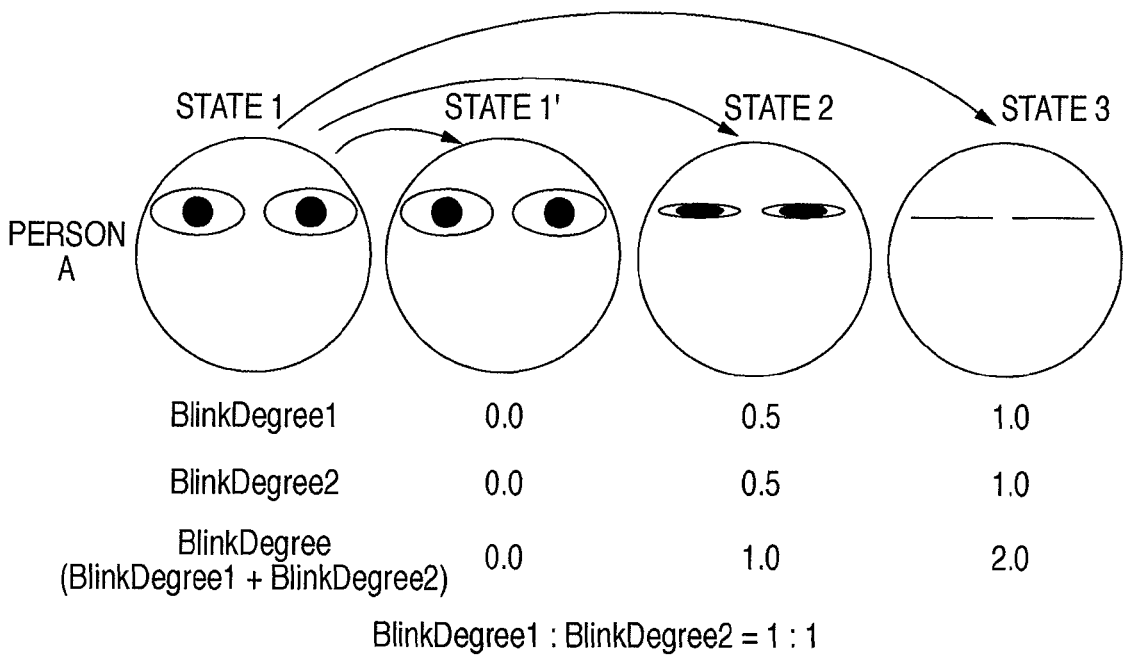
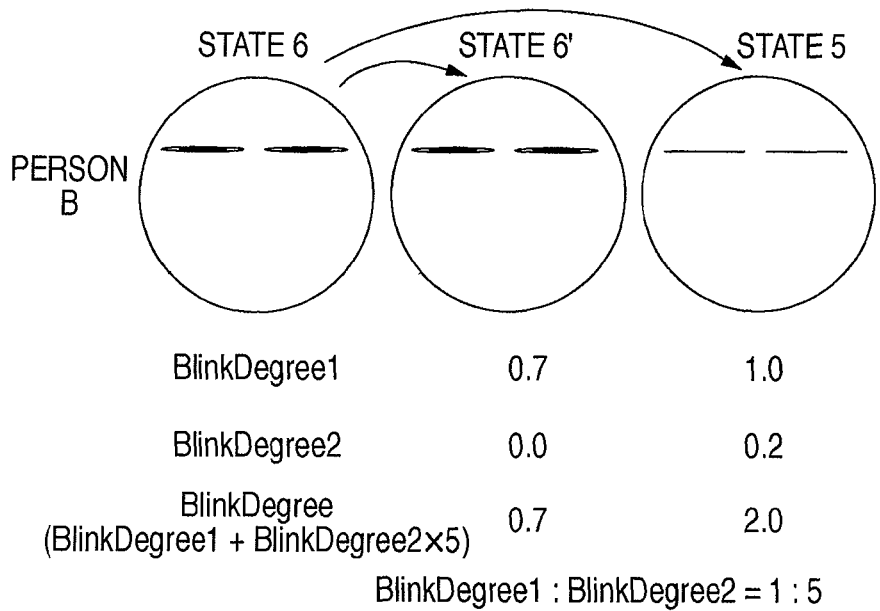

FIG. 20
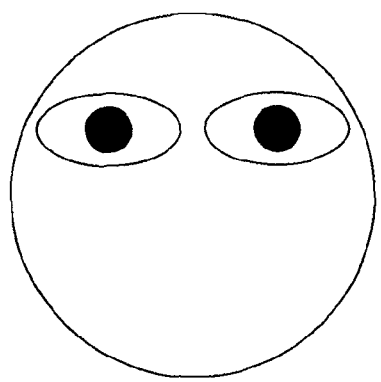 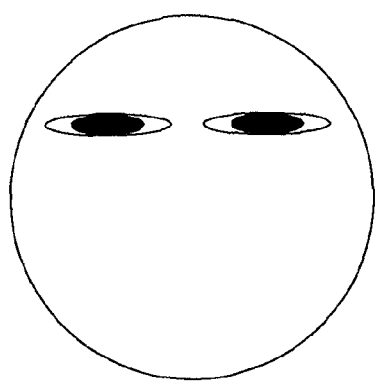
STATE 1
BLACK EYE AREA : 10
STATE 2
BLACK EYE AREA : 5
[DETERMINATION RESULTS]
STILL IMAGE DETERMINATION
(THRESHOLD 6): EYE CLOSED
CHANGE AMOUNT DETERMINATION
(THRESHOLD 4): EYE CLOSED
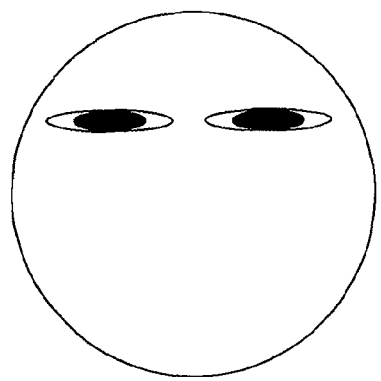 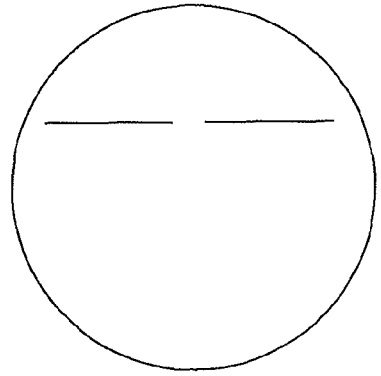
STATE 4
BLACK EYE AREA : 5
STATE 5
BLACK EYE AREA : 0
[DETERMINATION RESULTS]
STILL IMAGE DETERMINATION
(THRESHOLD 6): EYE CLOSED
CHANGE AMOUNT DETERMINATION
(THRESHOLD 4): EYE CLOSED

INFORMATION PROCESSING APPARATUS, EYE OPEN/CLOSED DEGREE DETERMINATION METHOD, COMPUTER-READABLE STORAGE MEDIUM, AND IMAGE SENSING APPARATUS

BACKGROUND OF THE INVENTION

1. Field of the Invention

The present invention relates to an information processing apparatus, eye open/closed degree determination method, computer-readable storage medium, and image sensing apparatus.

2. Description of the Related Art

A technique of detecting a face from an image including still and moving images has conventionally been known (Mitarai, Y., Mori, K., Matsugu, M. "Robust Face Detection System Based on Convolutional Neural Networks Using Selective Activation of Modules", FIT (Forum of Information Technology), L1-013, 2003). Further, techniques have been proposed for determining the open/closed degree of eyes in a detected face.

In this regard, Japanese Patent Laid-Open No. 09-044685 proposes a technique of comparing the distance between the eyebrow and the pupil or the area ratio of the eyebrow and pupil with a predetermined reference, and calculating the change amount of the distance, thereby determining the eye open/closed degree.

Japanese Patent Laid-Open No. 11-242744 proposes a technique of grouping eye regions into a white region and black (pupil) region, and when the black region changes, determining that the object blinks.

Japanese Patent Laid-Open No. 2004-192551 proposes a technique of preparing a plurality of processes to determine the eye open/closed degree in order to distinguish an eye state immediately before closing eyes from an eye state upon a change of the expression such as a smile, and determining the eye open/closed degree on the basis of a result using the ANDs of respective determination results.

There is an individual difference in eye size (e.g., the distance between upper and lower eyelids or the appearance of the pupil) in an expressionless state while the eyes are fully open. For example, the pupil of person A shown in FIG. 19 is completely seen in an expressionless state (state 1) while the eyes are fully opened. In contrast, the pupil of person B shown in FIG. 19 is partially hidden in an expressionless state (state 4) while the eyes are fully opened.

In this manner, there is an individual difference in eye size in an expressionless state. If the eye open/closed degree is determined from only one image, state 2 of person A shown in FIG. 19 and state 4 of person B shown in FIG. 19 are determined to have the same eye open/closed degree. For example, when state 2 of person A shown in FIG. 19 is determined as a shooting failure upon shooting by an image sensing apparatus, state 4 of person B shown in FIG. 19 is also determined as a shooting failure.

When determining the eye open/closed degree using the amount of change between a plurality of images, the amount of change from state 1 to state 2 of person A shown in FIG. 19 equals that of change from state 4 to state 5 of person B shown in FIG. 19. It is determined that state 2 of person A and state 5 of person B are the same. For example, when state 2 of person A shown in FIG. 19 is determined as a shooting success upon shooting by an image sensing apparatus, state 5 of person B shown in FIG. 19 is also determined as a shooting success.

Determination of whether an image shot by an image sensing apparatus is a failure or success changes depending on the user of the image sensing apparatus. It is necessary to detect the eye open/closed degree at high precision regardless of individual differences in the eye size. For example, the above-mentioned technique disclosed in Japanese Patent Laid-Open No. 2004-192551 determines the eye open/closed degree by using a combination of eye open/closed degree determination results. However, each eye open/closed degree determination result is a binary output representing that the eyes are open or closed. For this reason, even this technique cannot detect the eye open/closed degree at high precision regardless of individual differences in eye size.

A case where the eye open/closed degree is determined by a method using one image, and a case where it is determined by a method using the amount of change between a plurality of images will be examined. A case where the eye open/closed degree is determined when it changes from state 1 to state 2 shown in FIG. 20, and a case where the eye open/closed degree is determined when it changes from state 4 to state 5 shown in FIG. 20 will be exemplified.

When the eyes change from state 1 (black eye area 10) to state 2 (black eye area 5) shown in FIG. 20, the change amount of the black eye area is 5, and the absolute amount of the black eye area in state 2 is 5. When an absolute amount threshold for determining that the eyes are closed is set to 6 (it is determined that the eyes are closed when the absolute amount is smaller than 6), and a change amount threshold for determining that the eyes are closed is set to 4 (it is determined that the eyes are closed when the change amount is larger than 4), both determination results based on the absolute amount and change amount represent that the eyes are closed. When the eyes change from state 4 (black eye area 5) to state 5 (black eye area 0) shown in FIG. 20 and the same determinations as those described above are made, the same results are obtained, and both determination results based on the absolute amount and change amount represent that the eyes are closed. In this manner, according to the conventionally proposed eye open/closed degree determination method, state 2 and state 5 shown in FIG. 20 are determined to have the same eye open/closed degree.

SUMMARY OF THE INVENTION

The present invention enables to provide an information processing apparatus, eye open/closed degree determination method, computer-readable storage medium, and image sensing apparatus capable of detecting the eye open/closed degree at high precision regardless of individual differences in eye size.

According to a first aspect of the present invention there is provided an information processing apparatus comprising: an input unit configured to input an image; a face detection unit configured to detect a face of a person from the image input from the input unit; a first calculation unit configured to calculate a feature amount associated with an eye open/closed state from the face detected by the face detection unit; a second calculation unit configured to calculate, as a feature-change amount, a difference between the feature amount calculated by the first calculation unit and a feature amount calculated from a face detected from an image input before a predetermined time; and a third calculation unit configured to calculate an eye open/closed degree of eyes of the face detected by the face detection unit on the basis of the feature amount and the feature-change amount.

According to a second aspect of the present invention there is provided an eye open/closed degree determination method comprising: inputting an image;

detecting a face of a person from the image input in the inputting the image; calculating a feature amount associated with an eye open/closed state from the face detected in the detecting the face; calculating, as a feature-change amount, a difference between the feature amount calculated in the calculating the feature amount and a feature amount calculated from a face detected from an image input before a predetermined time; and calculating an eye opening/closing degree of eyes of the face detected in the detecting the face on the basis of the feature amount and the feature-change amount.

According to a third aspect of the present invention there is provided a computer-readable storage medium storing a computer program, the program causing a computer to function as an input unit configured to input an image, a face detection unit configured to detect a face of a person from the image input from the input unit, a first calculation unit configured to calculate a feature amount associated with an eye open/closed state from the face detected by the face detection unit, a second calculation unit configured to calculate, as a feature-change amount, a difference between the feature amount calculated by the first calculation unit and a feature amount calculated from a face detected from an image input before a predetermined time, and a third calculation unit configured to calculate an eye open/closed degree of eyes of the face detected by the face detection unit on the basis of the feature amount and the feature-change amount.

According to a fourth aspect of the present invention there is provided an image sensing apparatus comprising: an input unit configured to input an image; a face detection unit configured to detect a face of a person from the image input from the input unit; a first calculation unit configured to calculate a feature amount associated with an eye open/closed state from the face detected by the face detection unit; a second calculation unit configured to calculate, as a feature-change amount, a difference between the feature amount calculated by the first calculation unit and a feature amount calculated from a face detected from an image input before a predetermined time; a third calculation unit configured to calculate an eye open/closed degree of eyes of the face detected by the face detection unit on the basis of the feature amount and the feature-change amount; a determination unit configured to perform eye open/closed determination by performing threshold processing for the eye open/closed degree calculated by the third calculation unit; and an image sensing unit configured to shoot on the basis of a result of eye open/closed degree determination by the determination unit.

Further features of the present invention will be apparent from the following description of exemplary embodiments with reference to the attached drawings.

BRIEF DESCRIPTION OF THE DRAWINGS

FIG. 9 is a first view for explaining an example of the effects of the first embodiment;

FIG. 13 is a first view for explaining an example of the effects of the second embodiment;

FIG. 17 is a first view for explaining an example of the effects of the third embodiment;

FIG. 18 is a second view for explaining an example of the effects of the third embodiment;

FIG. 20 is a second view for explaining the conventional problem.

DESCRIPTION OF THE EMBODIMENTS

Preferred embodiments of the present invention will now be described in detail with reference to the drawings. It should be noted that the relative arrangement of the components, the numerical expressions and numerical values set forth in these embodiments do not limit the scope of the present invention unless it is specifically stated otherwise.

First Embodiment

Figure 1:
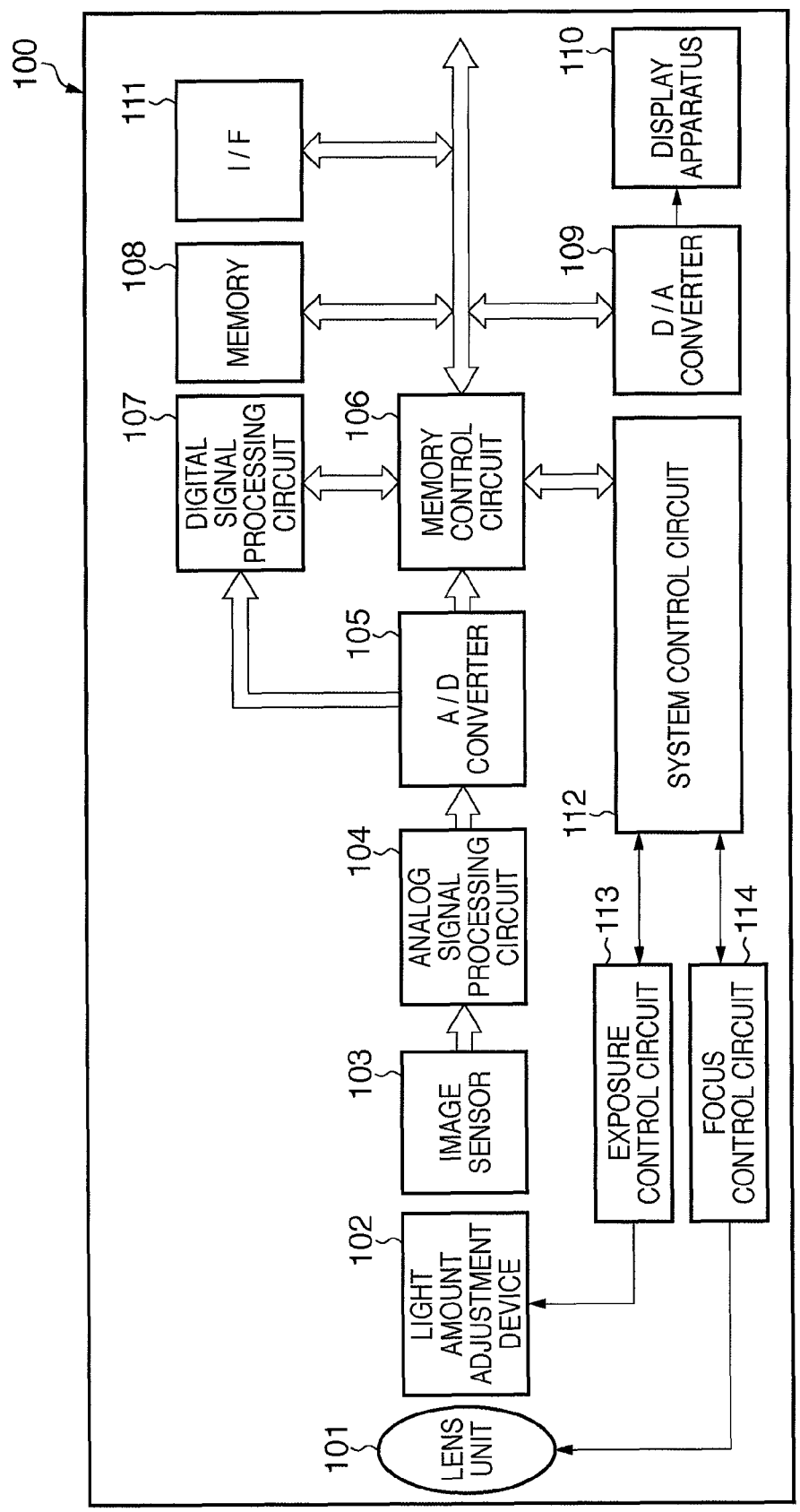
FIG. 1 is a block diagram showing an example of the arrangement of an image sensing apparatus 100 according to an embodiment of the present invention.

FIG. 1 is a block diagram showing an example of the arrangement of an image sensing apparatus 100 according to an embodiment of the present invention. The first embodiment will exemplify a case where the image sensing apparatus 100 is an electronic still camera.

The image sensing apparatus 100 includes an image sensing lens unit 101, and a light amount adjustment device 102 having a stop and shutter. An image sensor 103 is, for example, a CCD (Charge-Coupled Device) or CMOS (Complementary Metal Oxide Semiconductor) sensor for converting a light beam of an object image having passed through the image sensing lens unit into an electrical signal. An analog signal processing circuit 104 performs clamp, gain, and the like for an analog signal output from the image sensor 103. An A/D converter 105 converts an output from the analog signal processing circuit 104 into a digital signal.

A digital signal processing circuit 107 performs predetermined pixel interpolation, color conversion, and the like for data from the A/D converter 105 or data from a memory control circuit 106. The digital signal processing circuit 107 also performs predetermined arithmetic using sensed image data, and TTL AWB (Auto White Balance) processing based on the obtained arithmetic result. Further, the digital signal processing circuit 107 executes specific object face detection and eye open/closed degree determination for the sensed image data. The specific object face detection and eye open/closed degree determination use data stored in a memory (a memory 108 to be described later).

A system control circuit 112 performs TTL (Through The Lens) AF (Auto Focus), AE (Auto Exposure), and EF (pre-Electronic Flash) on the basis of the above-mentioned arithmetic results to control an exposure control circuit 113 and focus control circuit 114.

The memory control circuit 106 controls the analog signal processing circuit 104, the A/D converter 105, the digital signal processing circuit 107, the memory 108, and a digital/analog (to be referred to as D/A hereinafter) converter 109. Data A/D-converted by the A/D converter 105 is written in the memory 108 via the digital signal processing circuit 107 and memory control circuit 106. Data A/D-converted by the A/D converter 105 is sometimes written in the memory 108 directly via the memory control circuit 106.

The memory 108 stores, for example, data to be displayed on a display apparatus 110. Data stored in the memory 108 is output to the display apparatus 110 such as a TFT or LCD via the D/A converter 109, and displayed on it. The memory 108 stores images including sensed still images and moving images. The memory 108 has a capacity enough to store a predetermined number of still images and a moving image of a predetermined time. Even in continuous shooting or panoramic shooting of successively shooting a plurality of still images, many images can be written in the memory 108 at high speed. The memory 108 is also available as the work area of the system control circuit 112. Sensed still images and moving images may also be written in a storage medium such as a CD-ROM, floppy disk®, hard disk, magnetic tape, magneto-optical disk, or nonvolatile memory card by using an interface (I/F) 111.

The display apparatus 110 can sequentially display sensed image data, and in this case, functions as an electronic viewfinder. The display apparatus 110 can arbitrarily turn on/off the display in accordance with an instruction from the system control circuit 112. When the display is turned off, power consumption of the image sensing apparatus 100 can be reduced more greatly than when the display is ON. The display apparatus 110 displays an operating state, message, and the like using a text, image, or the like in accordance with execution of a program in the system control circuit 112.

The I/F 111 interfaces the image sensing apparatus 100 with a storage medium such as a memory card or hard disk. By using the I/F 111, the image sensing apparatus 100 can exchange image data and management information accessory to the image data with another computer or a peripheral device such as a printer. When the I/F 111 complies with the standard of a PCMCIA card, CF (Compact Flash®) card, or the like, the I/F 111 functions as a communication interface upon connecting various communication cards. These communication cards include a LAN card, modem card, USB card, IEEE1394 card, P1284 card, SCSI card, and PHS communication card.

The system control circuit 112 controls the overall operation of the image sensing apparatus 100. The memory in the system control circuit 112 stores constants, variables, programs, and the like for operating the system control circuit 112, or recognizing the face of a specific object and the eye open/closed degree. The Constants, variables, programs, and the like stored in the internal memory of the system control circuit 112 can be changed using a CD-ROM, floppy disk®, hard disk, magnetic tape, magneto-optical disk, nonvolatile memory card, or the like.

The exposure control circuit 113 controls the stop and shutter of the light amount adjustment device 102. The focus control circuit 114 controls focusing and zooming of the image sensing lens unit 101. The exposure control circuit 113 and focus control circuit 114 are controlled by TTL. The system control circuit 112 controls the exposure control circuit 113 and focus control circuit 114 on the basis of the result of executing calculation for sensed image data by the digital signal processing circuit 107.

Figure 2A:
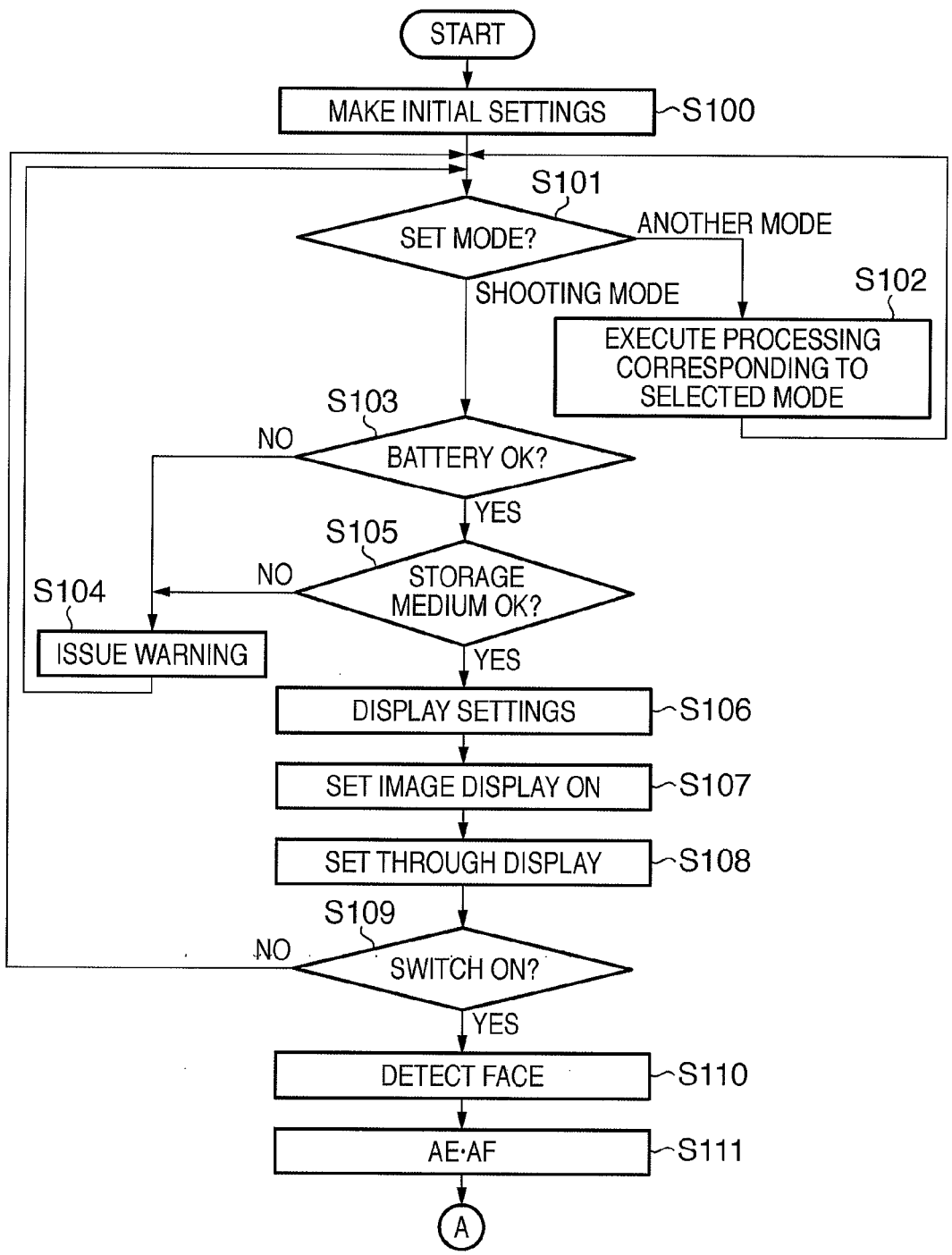
FIGS. 2A and 2B are a flowchart showing an example of a processing sequence in the image sensing apparatus 100 shown in FIG. 1.
Figure 2B:
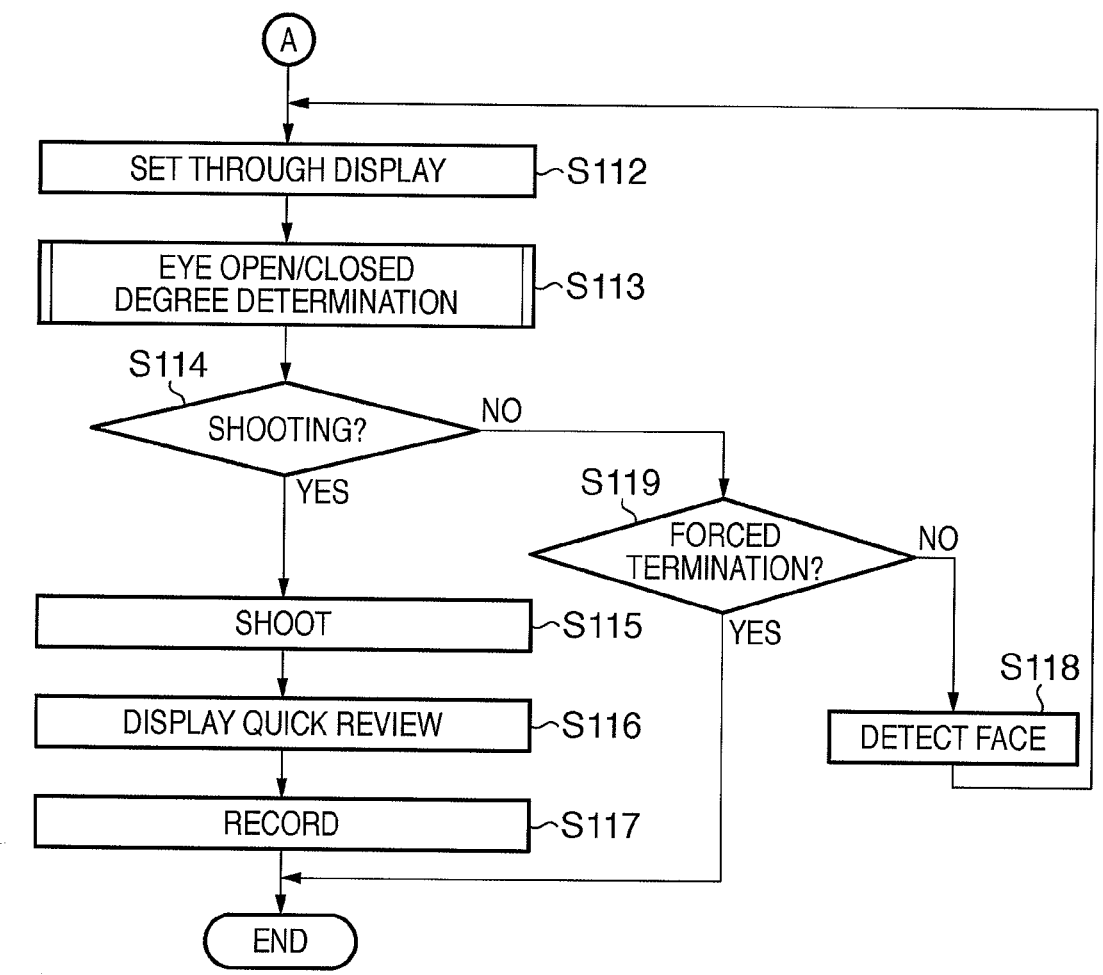

An example of a processing sequence in the image sensing apparatus 100 shown in FIG. 1 will be explained with reference to FIGS. 2A and 2B. A program for executing this processing is stored in, for example, the internal memory of the system control circuit 112, and executed under the control of the system control circuit 112.

This processing starts upon power-on or the like. When the processing starts, the system control circuit 112 initializes various flags, control variables, and the like in the internal memory (step S100). Then, the system control circuit 112 detects the mode setting state of the image sensing apparatus 100. An example of the mode is an eye closing prevention shooting mode.

If the system control circuit 112 detects a mode other than a shooting mode (another mode in step S101), the image sensing apparatus 100 executes processing corresponding to the selected mode (step S102), and then the process returns to step S101. If the system control circuit 112 detects a shooting mode such as the eye closing prevention shooting mode (shooting mode in step S101), it determines whether an error has occurred in the remaining battery level or operating state. If an error has occurred (NO in step S103), the system control circuit 112 issues a predetermined warning by an image or sound using the display apparatus 110 (step S104), and then the process returns to step S101. If no error has occurred (YES in step S103), the system control circuit 112 determines whether the storage medium operating state is improper for the operation of the image sensing apparatus 100, particularly an image data recording/playback operation to the storage medium.

If the storage medium operating state is improper (NO in step S105), the system control circuit 112 issues a predetermined warning by an image or sound using the display apparatus 110 similarly to the above-mentioned warning (step S104), and then the process returns to step S101. If the storage medium is proper (YES in step S105), the system control circuit 112 displays a user interface (to be referred to as a UI hereinafter) representing various setting states of the image sensing apparatus 100 by an image or sound using the display apparatus 110 (step S106). When the image display of the display apparatus 110 is ON, the UI representing various setting states of the image sensing apparatus 100 may also be displayed by an image or sound using the display apparatus 110. In this fashion, the user makes various settings.

The system control circuit 112 sets ON the image display of the display apparatus 110 (step S107). The system control circuit 112 sets a through display state to sequentially display sensed image data (step S108). In the through display state, the display apparatus 110 sequentially displays data written in the memory 108, implementing an electronic viewfinder function.

After that, the image sensing apparatus 100 determines whether the user such as a photographer has pressed the shutter switch. If the user has not pressed the shutter switch (NO in step S109), the process returns to step S101. If the user has pressed the shutter switch (YES in step S109), the system control circuit 112 executes face detection (step S110). In the face detection, image data input from the image sensor 103 is compressed to low resolution, and the face of a person is detected from the compressed image data. More specifically, image data is compressed to a low resolution of, for example, 640×480 pixels by executing thinning or the like, and then a face is detected. A known example of the face detection method is convolutional neural network (CNN) of hierarchically detecting high-order features such as an eye and mouth from low-order features such as an edge, and finally detecting the barycenter of the face (Mitarai, Y., Mori, K., Matsugu, M. "Robust Face Detection System Based on Convolutional Neural Networks Using Selective Activation of Modules", FIT (Forum of Information Technology), L1-013, 2003). By using the CNN, the barycenter of an eye or mouth can be obtained.

After detecting the face of a person in this way, the system control circuit 112 executes predetermined AE/AF control for the detected person's face (step S111), and through-displays a sensed image (step S112). At this time, the system control circuit 112 determines the eye open/closed degree of each person by using the eye/face position detected in step S110 (step S113). Details of the eye open/closed degree determination will be explained later.

The system control circuit 112 determines, based on the result of the eye open/closed degree determination, whether to shoot by the image sensing apparatus 100. More specifically, if the system control circuit 112 determines that the eyes are closed, it does not cause the image sensing apparatus 100 to shoot (No in step S114), and determines whether to forcibly terminate shooting. If the system control circuit 112 determines to forcibly terminate shooting (YES in step S119), the process ends. If the system control circuit 112 determines not to forcibly terminate shooting (NO in step S119), it performs face detection again (step S118), and the process returns to step S112.

If the system control circuit 112 determines that the eyes are open, it causes the image sensing apparatus 100 to shoot (step S115 after YES in step S114). After shooting, the system control circuit 112 displays a quick review of the sensed image (step S116), encodes the sensed high-resolution image, and records the encoded image on a storage medium such as a flash memory (step S117). That is, a low-resolution image compressed by thinning or the like is used for face detection, whereas a high-resolution image is used for recording.

Figure 3:
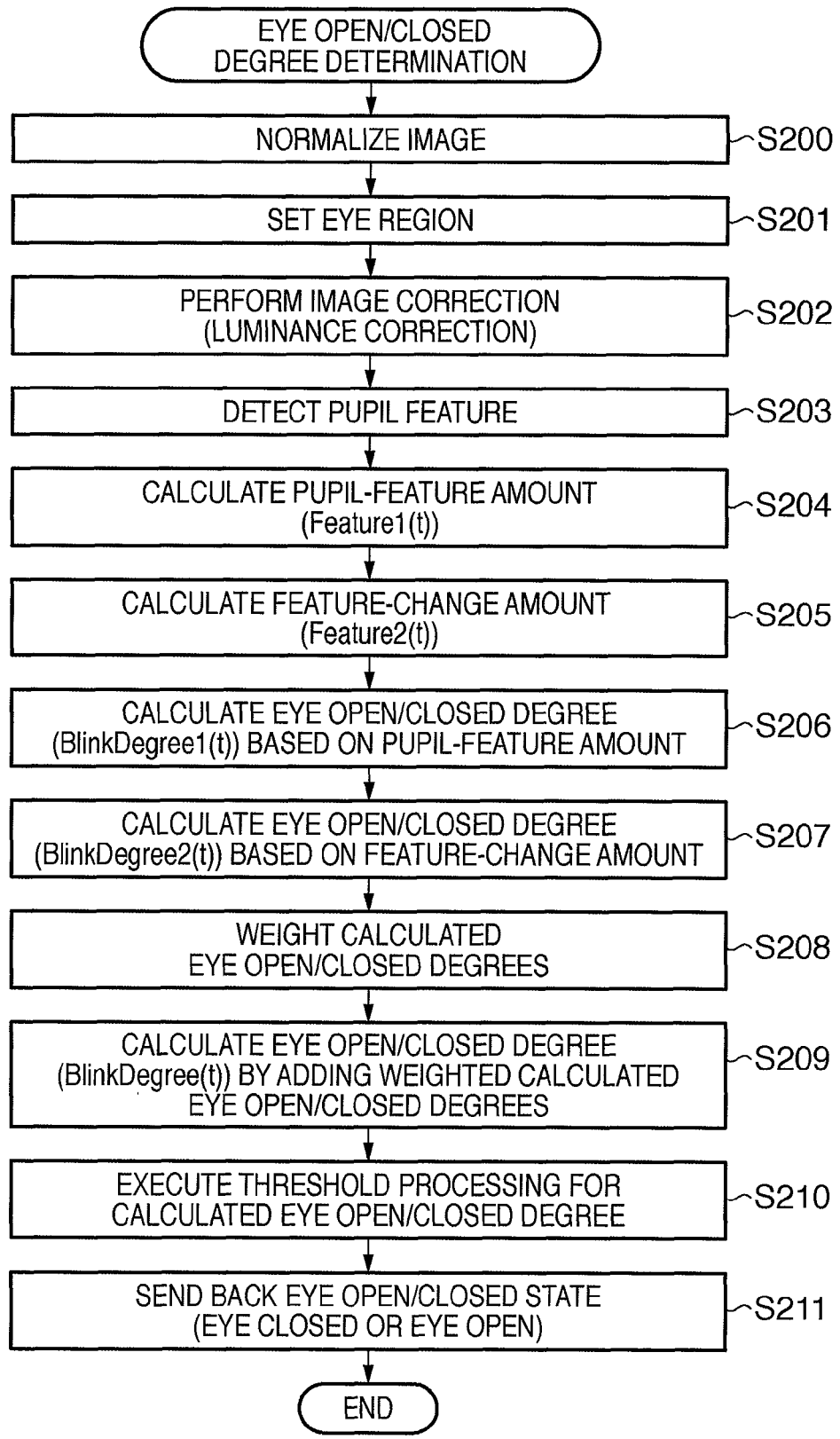
FIG. 3 is a flowchart showing an example of the sequence of eye open/closed degree determination in step S113 shown in FIG. 2B.

Details of the eye open/closed degree determination in step S113 shown in FIG. 2B will be explained with reference to FIG. 3.

Figure 4:
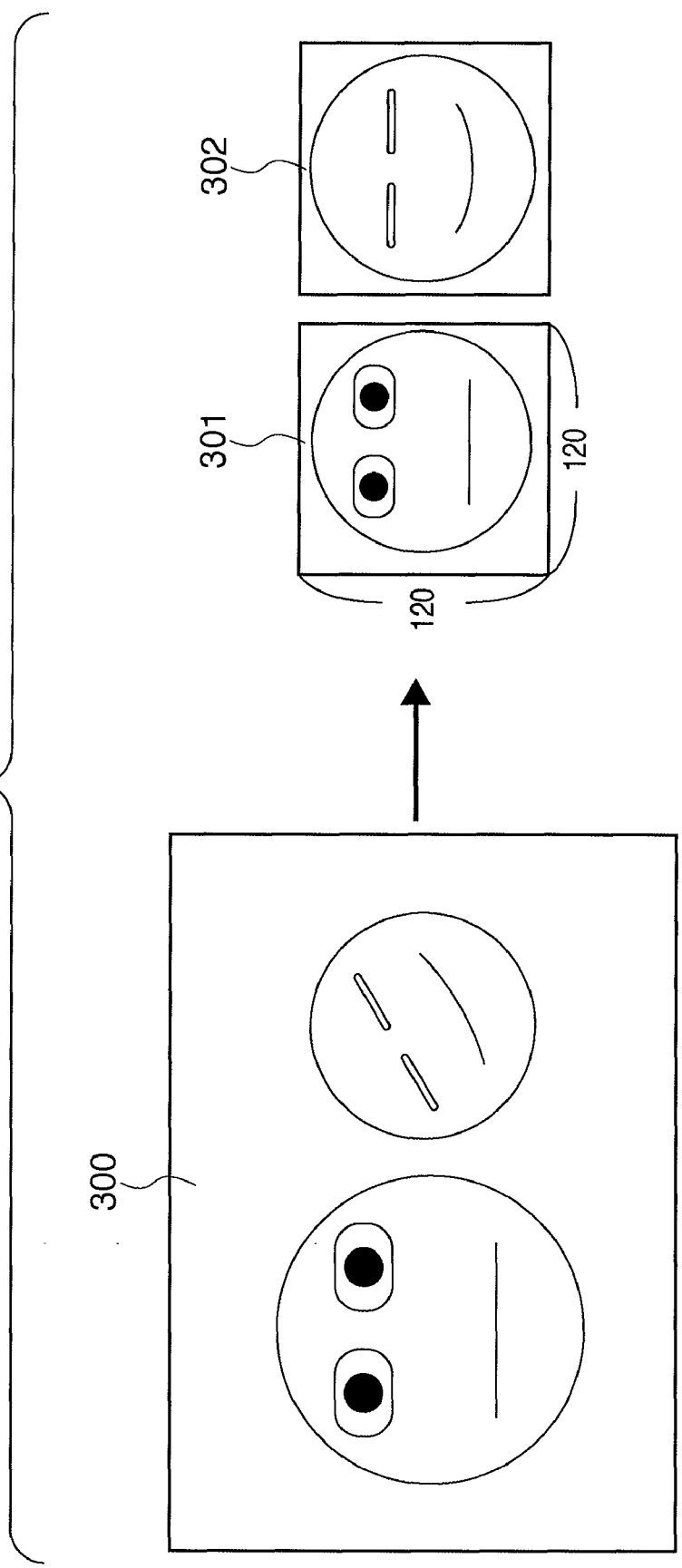
FIG. 4 is a view showing an example of an outline of image normalization.

When this processing starts, the system control circuit 112 executes image normalization using an eye or face position detected in step S110 (step S200). In the normalization, the orientation of each face in an input image 300 compressed to low resolution is aligned to be erect, as shown in FIG. 4. Then, affine transformation and extraction are done to change the width between two eyes to a predetermined number of pixels (e.g., 50 pixels) and change the width and height of an extracted image to a predetermined number of pixels (e.g., 120×120 pixels). In an example shown in FIG. 4, face images 301 and 302 are obtained as a result of normalizing the input image 300.

Figure 5:
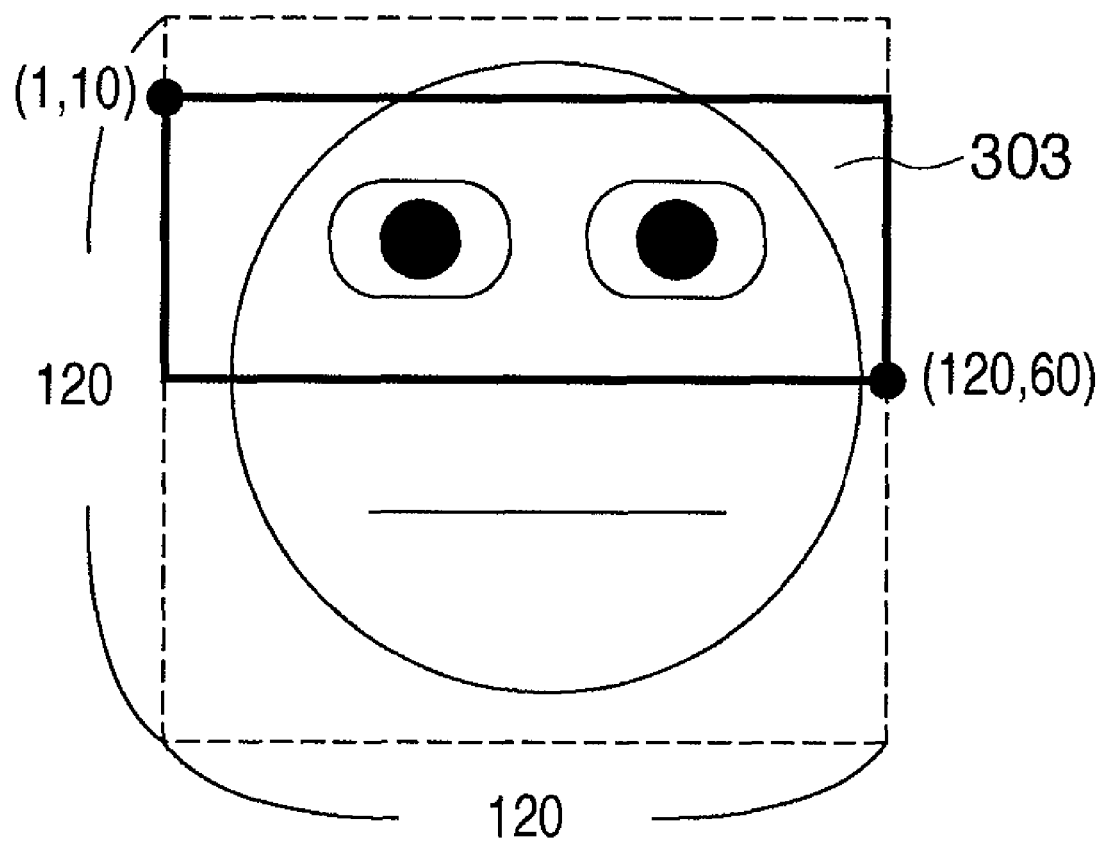
FIG. 5 is a view showing an example of an outline of processing when setting a region to undergo detection of a pupil feature.

Thereafter, the system control circuit 112 sets an eye region as shown in FIG. 5 in the normalized image (step S201). In an example shown in FIG. 5, the coordinate point of the upper left corner of an eye region 303 is set to (1,10), and that of its lower right corner is set to (120,60).

After setting the eye region, the system control circuit 112 performs image correction (e.g., luminance correction) for the eye region (step S202). In the luminance correction, the luminance histogram of the eye region is created and expanded to change the luminance value of each pixel.

Figure 6:
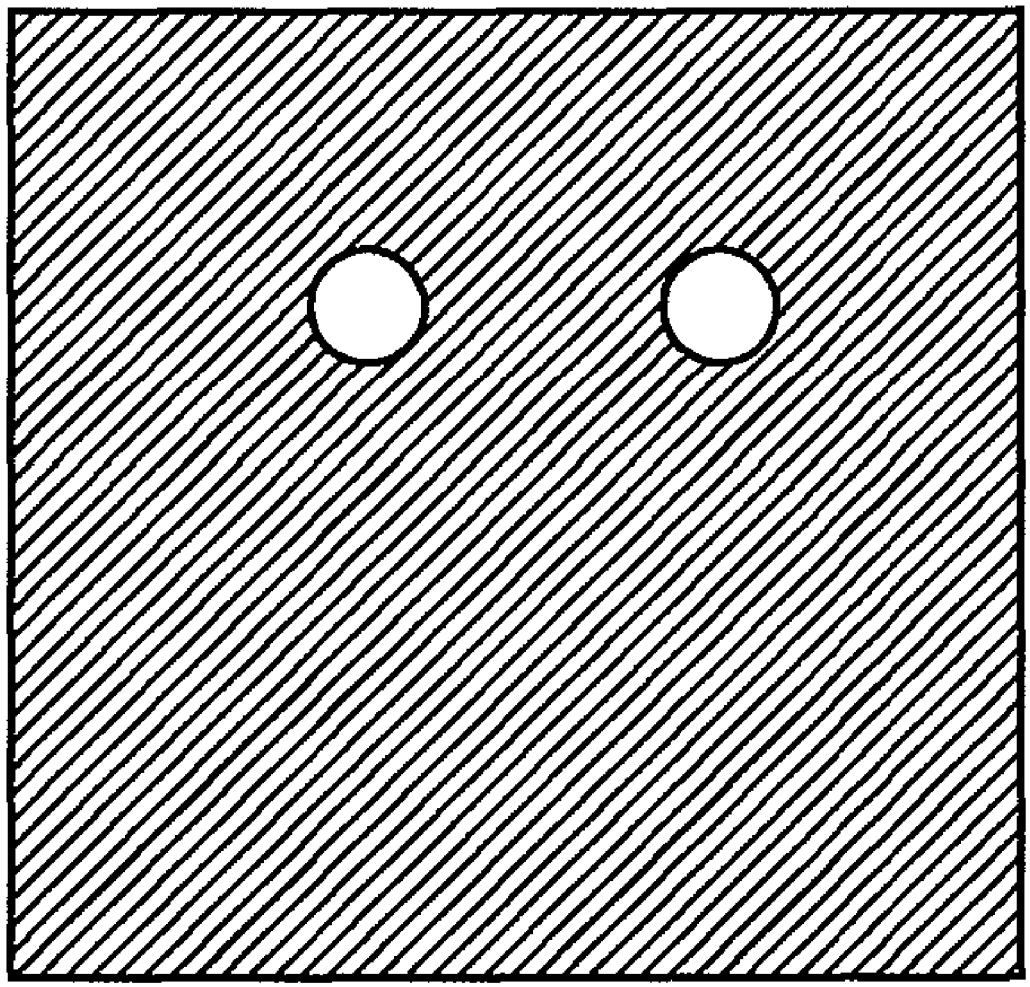
FIG. 6 is a view showing an example of a pupil feature detection result.

After the luminance correction, the system control circuit 112 detects a pupil feature from the eye region of the luminance-corrected image (step S203). The pupil feature is detected using a pupil detection CNN which has learned in advance to detect the pupil, similar to face detection. The pupil detection CNN is given a pupil region as a right answer and a region other than the pupil region as a wrong answer, and learns to output a large value from each neuron of the CNN in only a region where the pupil exists. If the image having undergone luminance correction in step S202 is input to the pupil detection CNN, for example, neuron output values as shown in FIG. 6 are obtained.

Then, the system control circuit 112 calculates a pupil-feature amount using the pupil-feature detection amount (step S204). The pupil-feature amount in the first embodiment is represented by an output value counter(t) which becomes equal to or larger than a predetermined threshold $I_{th}$ at time t[s]:

$$\text{if } I(x,y) \geq I_{th} \Rightarrow \text{Counter}(t) += 1 \quad (1)$$

Instead of the pupil-feature amount, the distance between edges corresponding to upper and lower eyelids is also available. A pupil-feature amount extracted from one image to undergo determination of the eye open/closed degree is represented by Feature1(t):

$$\text{Feature1}(t) = \text{Counter}(t) \quad (2)$$

After the feature amount calculation, the system control circuit 112 calculates a feature-change amount Feature2(t) of the calculated pupil-feature amount Feature1(t) (step S205). The feature-change amount Feature2(t) is calculated by calculating the difference between the pupil-feature amount Feature1(t) and a predetermined feature amount (in this case, a previously calculated pupil-feature amount Feature1($t_n$):

$$\text{Feature2}(t) = |\text{Counter}(t_n) - \text{Counter}(t)| \quad (3)$$

The previously calculated pupil-feature amount Feature1($t_n$) is a pupil-feature amount calculated a predetermined time (e.g., 500 ms) before calculating the pupil-feature amount Feature1(t). In equation (3), n is an average time when the man blinks unconsciously. For example, when the average time when the man closes an open eye is 500 ms, n=500 ms is set.

After the feature-change amount calculation, the system control circuit 112 calculates eye open/closed degrees for the calculated pupil-feature amount Feature1(t) and feature-change amount Feature2(t), respectively (steps S206 and S207). In the first embodiment, the eye open/closed degree will be explained using an eye closing degree BlinkDegree(t). However, the eye open/closed degree may also be represented by the eye opening degree.

An eye open/closed degree BlinkDegree1(t) based on the pupil-feature amount Feature1(t) is calculated by substituting the pupil-feature amount Feature1(t) into a predetermined function $\text{func}_1$:

$$\text{BlinkDegree1}(t) = \text{func}_1(\text{Feature1}(t)) \quad (4)$$

An eye open/closed degree BlinkDegree2(t) based on the feature-change amount Feature2(t) is calculated by substituting the feature-change amount Feature2(t) into a predetermined function $func_2$:

$$BlinkDegree2(t) = func_2(Feature2(t)) \quad (5)$$

As represented by equation (6), the system control circuit 112 adds weights $w_1$ and $w_2$ to the eye open/closed degrees BlinkDegree1(t) and BlinkDegree2(t), and then adds the weighted eye open/closed degrees BlinkDegree1(t) and BlinkDegree2(t) (step S208), thereby calculating a final eye open/closed degree BlinkDegree(t) (step S209):

$$BlinkDegree(t) = w_1 \times BlinkDegree1(t) + w_2 \times BlinkDegree2(t) \quad (6)$$

where the weights $w_1$ and $W_2$ in the embodiment are 1:1.

Figure 7:
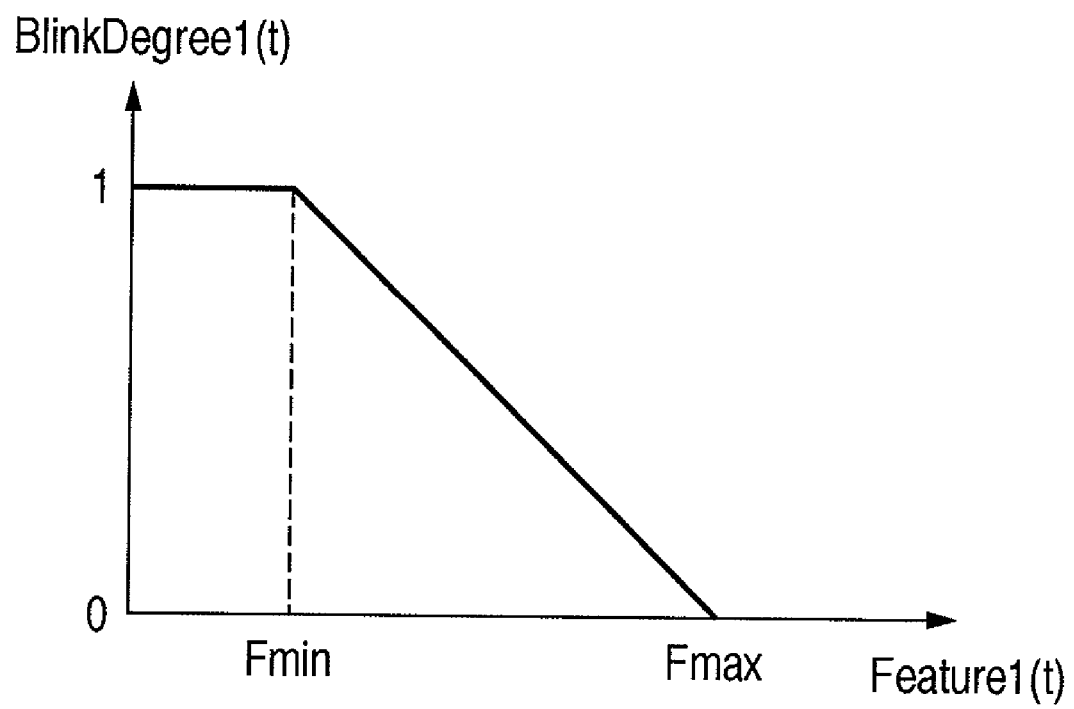
FIG. 7 is a graph showing an example of the distribution of eye open/closed degree values calculated by a predetermined function $func_1$.

FIG. 7 shows the distribution of eye open/closed degree values calculated by the predetermined function $func_1$. As shown in FIG. 7, as the pupil-feature amount Feature1(t) calculated from one image to undergo determination of the eye open/closed degree becomes larger, the eye open/closed degree BlinkDegree1(t) becomes smaller. That is, as the pupil-feature amount Feature1(t) becomes larger, the possibility of determining that the eyes are open becomes higher.

Figure 8:
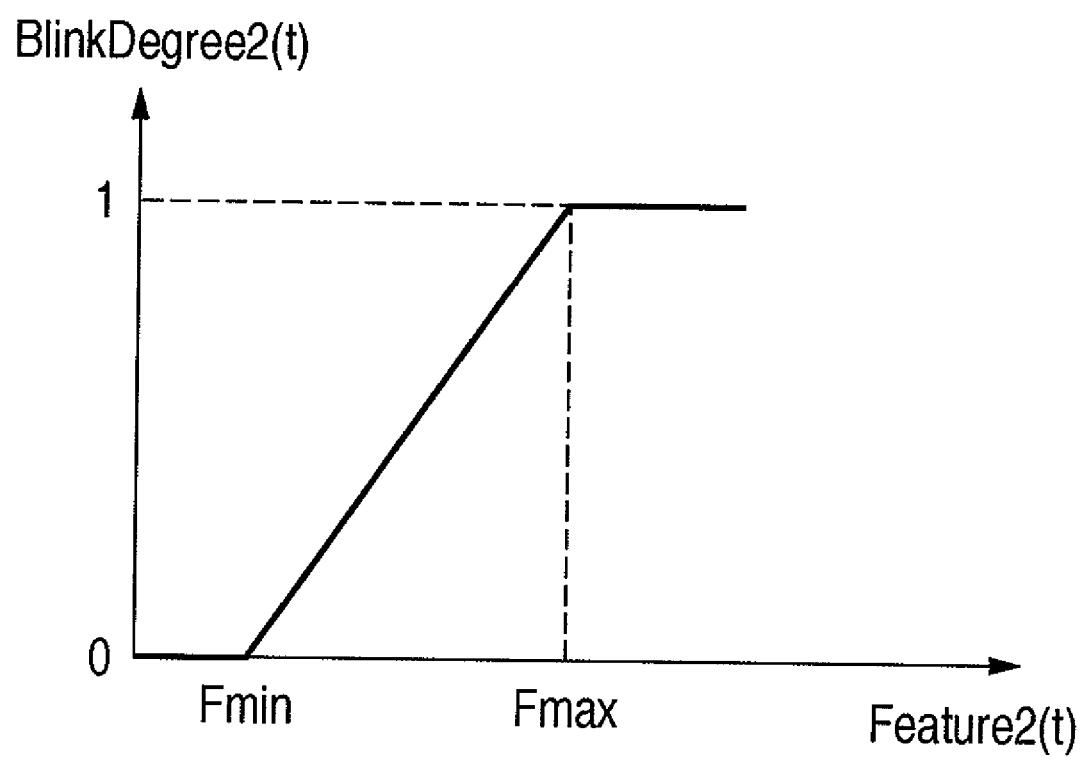
FIG. 8 is a graph showing an example of the distribution of eye open/closed degree values calculated by a predetermined function $func_2$.

FIG. 8 shows the distribution of eye open/closed degree values calculated by the predetermined function $func_2$. As shown in FIG. 8, as the feature-change amount Feature2(t) becomes larger, the eye open/closed degree BlinkDegree2(t) becomes larger. That is, as the feature-change amount Feature2(t) becomes larger, the possibility of determining that the eyes are kept closed or being opened or closed becomes higher.

Referring back to FIG. 3, after executing the final eye open/closed degree calculation, the system control circuit 112 makes a binary determination of whether the eyes are closed or open. This determination is achieved by executing threshold processing for the eye open/closed degree BlinkDegree(t) (step S210). The system control circuit 112 sends back a determination result "eyes open" or "eye closed" based on the relationship (equal to and larger or smaller than the threshold) between BlinkDegree(t) and the threshold (step S211). Then, the process ends.

Figure 10:
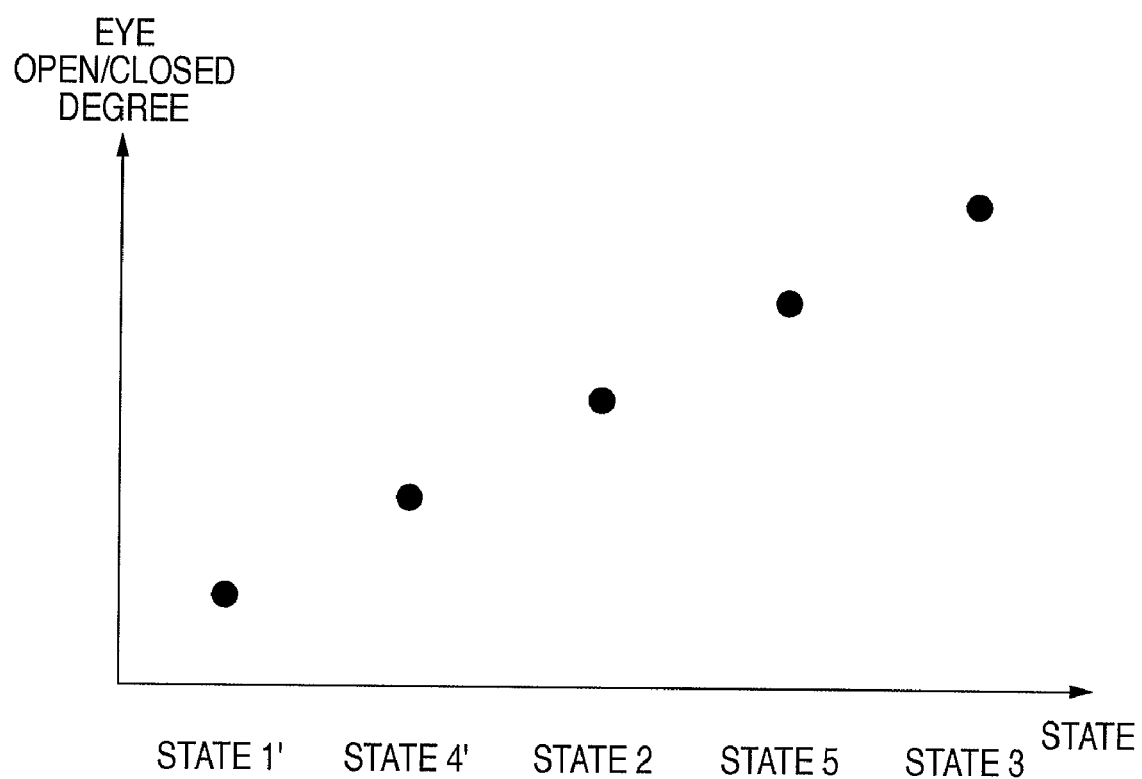
FIG. 10 is a second view for explaining an example of the effects of the first embodiment.

FIGS. 9 and 10 are views for explaining effects obtained using the pupil-feature amount Feature1(t) calculated from an image to undergo determination of the eye open/closed degree and the corresponding feature-change amount Feature2(t) when determining the eye open/closed state.

FIG. 9 is a view showing results of calculating the eye open/closed degrees in respective states of person A having a large eye open/closed width and those of person B having a small eye open/closed width. As described above, the eye open/closed degree BlinkDegree1(t) is calculated based on the pupil-feature amount Feature1(t) of an image to undergo determination of the eye open/closed degree. The eye open/closed degree BlinkDegree2(t) is calculated based on the feature-change amount Feature2(t) representing the difference between the pupil-feature amount Feature1(t) and the previously calculated pupil-feature amount Feature1 $(t_n)$. BlinkDegree (t) represents the final eye open/closed degree which is calculated by adding the weighted BlinkDegree1(t) and BlinkDegree2(t).

A case where the eyes of person A change from state 1 (eye open state) to state 1' (eye open state) will be examined. In this case, the pupil is clearly seen in state 1' (eye open state), so the pupil-feature amount Feature1(t) takes a large value. Hence, the eye open/closed degree BlinkDegree1(t) takes a small value. When the eyes of person A change from state 1 (eye open state) to state 1' (eye open state), the pupil-feature amount Feature1(t) hardly changes. Thus, the eye open/closed degree BlinkDegree2(t) calculated based on the feature-change amount Feature2(t) between the pupil-feature amount Feature1(t) and the previously calculated pupil-feature amount Feature1($t_n$) also takes a small value. As a result, the eye open/closed degree BlinkDegree(t) finally calculated after adding the weights=1:1 becomes "0.0".

A case where the eyes of person A change from state 1 (eye open state) to state 2 (eye half-open state) will be examined. In this case, the pupil region is partially seen in state 2 (eye half-open state), so the pupil-feature amount Feature1(t) takes an intermediate value (e.g., a value between 0 and 1). Hence, the eye open/closed degree BlinkDegree1(t) also takes an intermediate value. When the eyes of person A change from state 1 (eye open state) to state 2 (eye half-open state), the pupil-feature amount Feature1(t) slightly changes. Thus, the eye open/closed degree BlinkDegree2(t) calculated based on the feature-change amount Feature2(t) between the pupil-feature amount Feature1(t) and the previously calculated pupil-feature amount Feature1($t_n$) also takes an intermediate value. The eye open/closed degree BlinkDegree(t) finally calculated after adding the weights=1:1 becomes "1.0".

Similarly, a case where the eyes of person A change from state 1 (eye open state) to state 3 (eye closed state) will be examined. In this case, the eye open/closed degree BlinkDegree1(t) calculated based on the pupil-feature amount Feature1(t) takes a large value. Also, the eye open/closed degree BlinkDegree2(t) calculated based on the feature-change amount Feature2(t) also takes a large value. The eye open/closed degree BlinkDegree(t) finally calculated after adding the weights=1:1 becomes "2.0".

In contrast, a case where the eyes of person B change from state 4 (eye open state) to state 4' (eye open state) will be examined. In this case, the eye open/closed degree BlinkDegree1(t) calculated based on the pupil-feature amount Feature1(t) takes an intermediate value. The eye open/closed degree BlinkDegree2(t) calculated based on the feature-change amount Feature2(t) takes a small value. The eye open/closed degree BlinkDegree(t) finally calculated after adding the weights=1:1 becomes "0.5".

A case where the eyes of person B change from state 4 (eye open state) to state 5 (eye closed state) will be examined. In this case, the eye open/closed degree BlinkDegree1(t) calculated based on the pupil-feature amount Feature1(t) takes a large value. The eye open/closed degree BlinkDegree2(t) calculated based on the feature-change amount Feature2(t) takes an intermediate value. The eye open/closed degree BlinkDegree(t) finally calculated after adding the weights=1:1 becomes "1.5".

FIG. 10 shows the distribution of the calculated eye open/closed degree BlinkDegree(t). As shown in FIG. 10, calculated eye open/closed degrees in the respective states of persons A and B take different values. In other words, the eye open/closed degree can be detected at high precision regardless of individual differences in eye size.

As described above, according to the first embodiment, eye open/closed degrees calculated based on a pupil-feature amount obtained from an image to be determined, and a feature-change amount representing the difference between the pupil-feature amount and a previously calculated pupil-feature amount are weighted and added to calculate the final eye open/closed degree. As a result, the eye open/closed state can be detected at high precision regardless of individual differences in eye size.

In the above-described first embodiment, the final eye open/closed degree is calculated after weighting. However, weighting is not indispensable, and the final eye open/closed degree may also be calculated without weighting.

Second Embodiment

The second embodiment will now be explained. The arrangement of an apparatus and the sequence of the overall operation in the second embodiment are the same as those in FIGS. 1 and 2 described in the first embodiment, a description thereof will be omitted, and only differences from the first embodiment will be explained. The second embodiment is different from the first embodiment in eye open/closed degree determination described with reference to FIG. 3.

Figure 11:
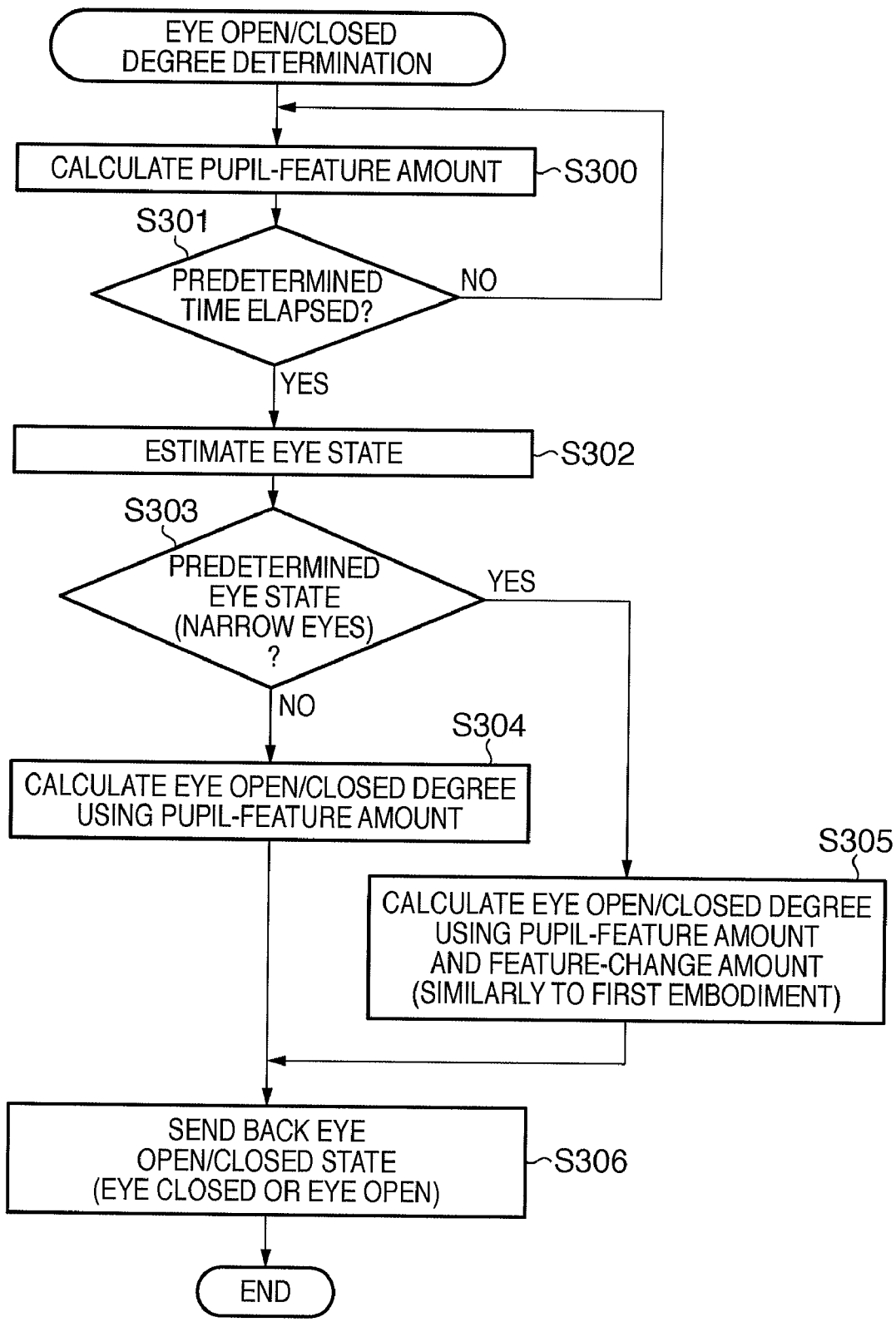
FIG. 11 is a flowchart showing an example of the sequence of eye open/closed degree determination according to the second embodiment.

The sequence of eye open/closed degree determination according to the second embodiment will be explained with reference to FIG. 11. In the second embodiment, to prevent a repetitive description, a description of detailed processing (e.g., methods of detecting and calculating a pupil-feature amount) described in the first embodiment will be omitted, and only a rough sequence representing the difference will be explained.

When this processing starts, a system control circuit 112 estimates a state in which the eyes of a face detected in step S110 (FIG. 2A) are open. More specifically, the system control circuit 112 estimates a state in which the eyes are open, and checks whether this eye state corresponds to a predetermined eye state (narrow eyes in the second embodiment). Even when a person with narrow eyes normally opens his eyes, most part of the pupil region is hidden.

To estimate an eye state when the eyes are open, the system control circuit 112 calculates a pupil-feature amount Feature1(t) by the same method as that in the first embodiment (step S300). The pupil-feature amount Feature1(t) is repetitively calculated till the lapse of a predetermined time (NO in step S301). That is, the system control circuit 112 calculates pupil-feature amounts Feature1(t) from respective frame images sequentially input within the predetermined time. The predetermined time is an average time taken to blink. It suffices to always blink within a predetermined time (e.g., 5 sec).

Upon the lapse of the predetermined time (YES in step S301), the system control circuit 112 estimates an eye state on the basis of the pupil-feature amount Feature1(t) calculated from a plurality of frame images in step S300 (step S302). More specifically, the system control circuit 112 estimates an eye open state by referring to pupil-feature amounts Feature1 $(t_1), \ldots,$ Feature1$(t_{n1})$ calculated within the predetermined time (time $t=t_1[s]$ to time $t=t_{n1}[s]$).

Figure 12:
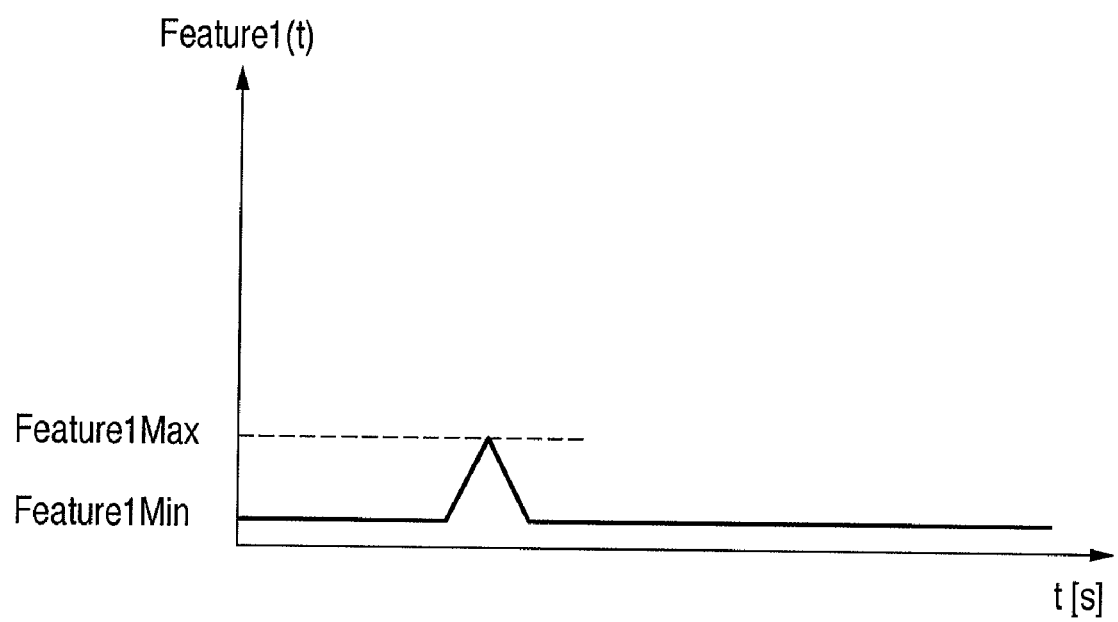
FIG. 12 is a graph showing an example of a change of the pupil-feature amount within a predetermined time.

FIG. 12 is a graph showing the pupil-feature amounts Feature1$(t_1), \ldots,$ Feature1$(t_{n1})$ calculated from time $t=t_1[s]$ to time $t=t_{n1}[s]$.

Whether the eyes correspond to a predetermined eye state (narrow eyes) is determined based on the width L (=Feature1Max−Feature1Min) of the pupil-feature amount Feature1(t) calculated from $t=t_1[s]$ to time $t=t_{n1}[s]$. More specifically, if the width L of the pupil-feature amount Feature1(t) is larger than a predetermined threshold $L_{th}$, it is determined that most part of the pupil region is not hidden when the eyes are open. If the width L of the pupil-feature amount Feature1(t) is equal to or smaller than the predetermined threshold $L_{th}$, it is determined that most part of the pupil region is hidden when the eyes are open.

If the eyes are not in the predetermined eye state (NO in step S303), the system control circuit 112 calculates BlinkDegree$(t_{n1})$ using only the pupil-feature amount Feature1$(t_{n1})$ calculated from one image at time $t=t_{n1}[s]$ (step S304). Calculating the eye open/closed degree BlinkDegree$(t_{n1})$ using only the pupil-feature amount Feature1$(t_{n1})$ equals setting the weight $w_2$ to 0.

If the system control circuit 112 determines that the eyes are in the predetermined eye state, that is, the eyes are narrow (YES in step S303), it calculates the eye open/closed degree by using both the pupil-feature amount and feature-change amount by the same method as that in the first embodiment (step S305). More specifically, the system control circuit 112 calculates the eye open/closed degree BlinkDegree$(t_{n1})$ by using the pupil-feature amount Feature1$(t_{n1})$ calculated from one image at time $t=t_{n1}[s]$ and the feature-change amount Feature2$(t_{n1})$. The feature-change amount Feature2$(t_{n1})$ represents the difference between the pupil-feature amount Feature1$(t_{n1})$ and a pupil-feature amount Feature1$(t_{n1-n1'})$ ($1 \leq n_1 < n_1$) calculated from a previously input image. In this case, the weights $w_1$ and $w_2$ are set to 1:1.

After that, the system control circuit 112 determines the eye open/closed state by executing threshold processing for the calculated eye open/closed degree BlinkDegree$(t_{n1})$, and sends back the determination result (eye closed or eye open) (step S306). Then, the process ends.

As described above, according to the second embodiment, if the eyes of a person, like person A shown in FIG. 13, are not in a predetermined eye state, that is, are not narrow, the eye open/closed degree BlinkDegree$(t_{n1})$ is calculated using only a feature amount obtained from one image. If the eyes of a person, like person B shown in FIG. 13, are in a predetermined eye state, that is, are narrow, the eye open/closed degree BlinkDegree$(t_{n1})$ is calculated using a feature amount obtained from one image and a feature-change amount. By switching the eye open/closed degree calculation method on the basis of eye state, the eye open/closed degree can be determined at high precision regardless of individual differences in eye size. Accordingly, high-precision detection of the eye open/closed degree can be achieved at minimum processing cost.

Third Embodiment

The third embodiment will be explained. The arrangement of an apparatus in the third embodiment is the same as that in FIG. 1 described in the first embodiment, a description thereof will be omitted, and only differences from the first embodiment will be explained.

Figure 14A:
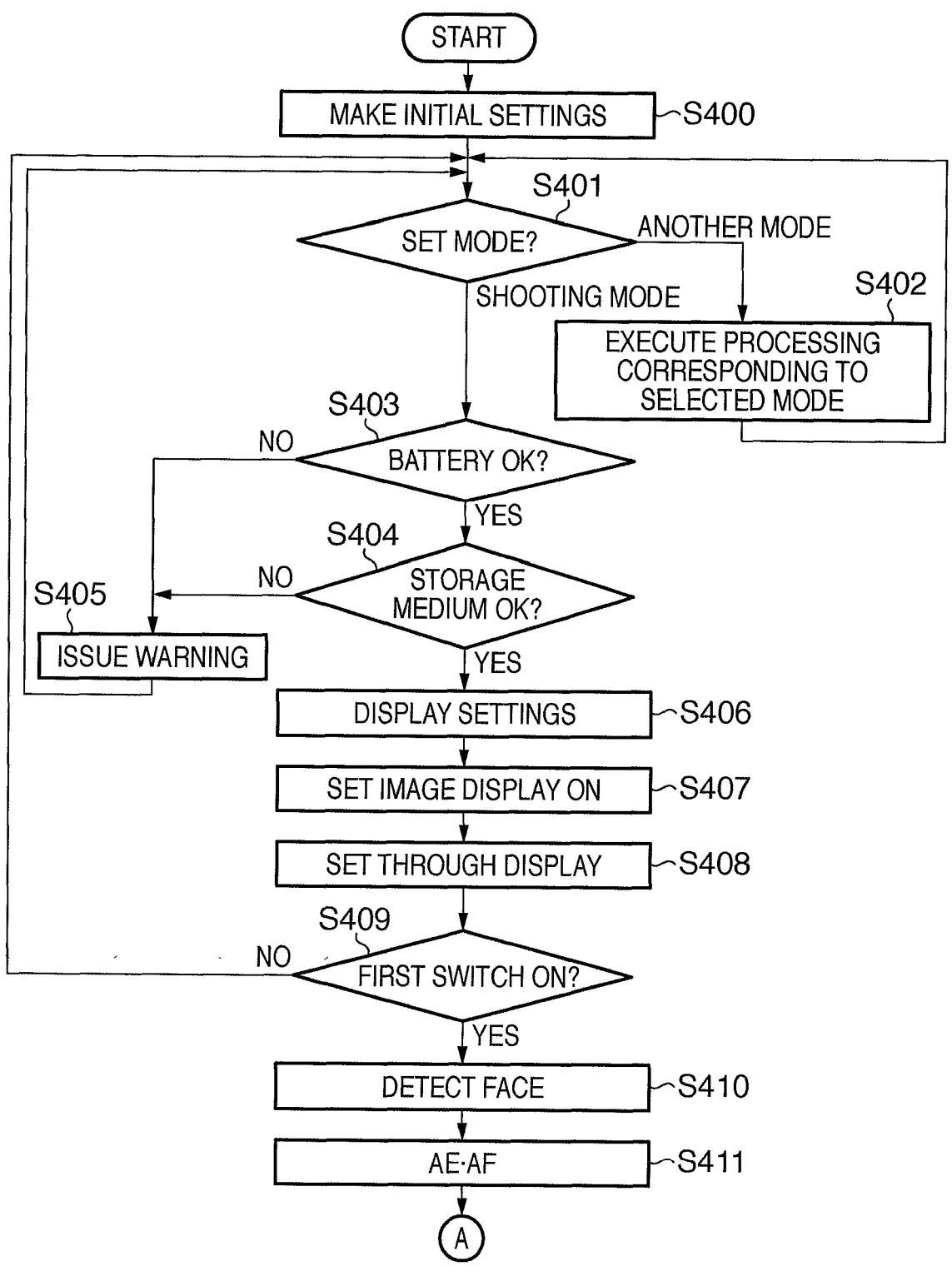
FIGS. 14A and 14B are a flowchart showing an example of a processing sequence in an image sensing apparatus 100 according to the third embodiment.
Figure 14B:
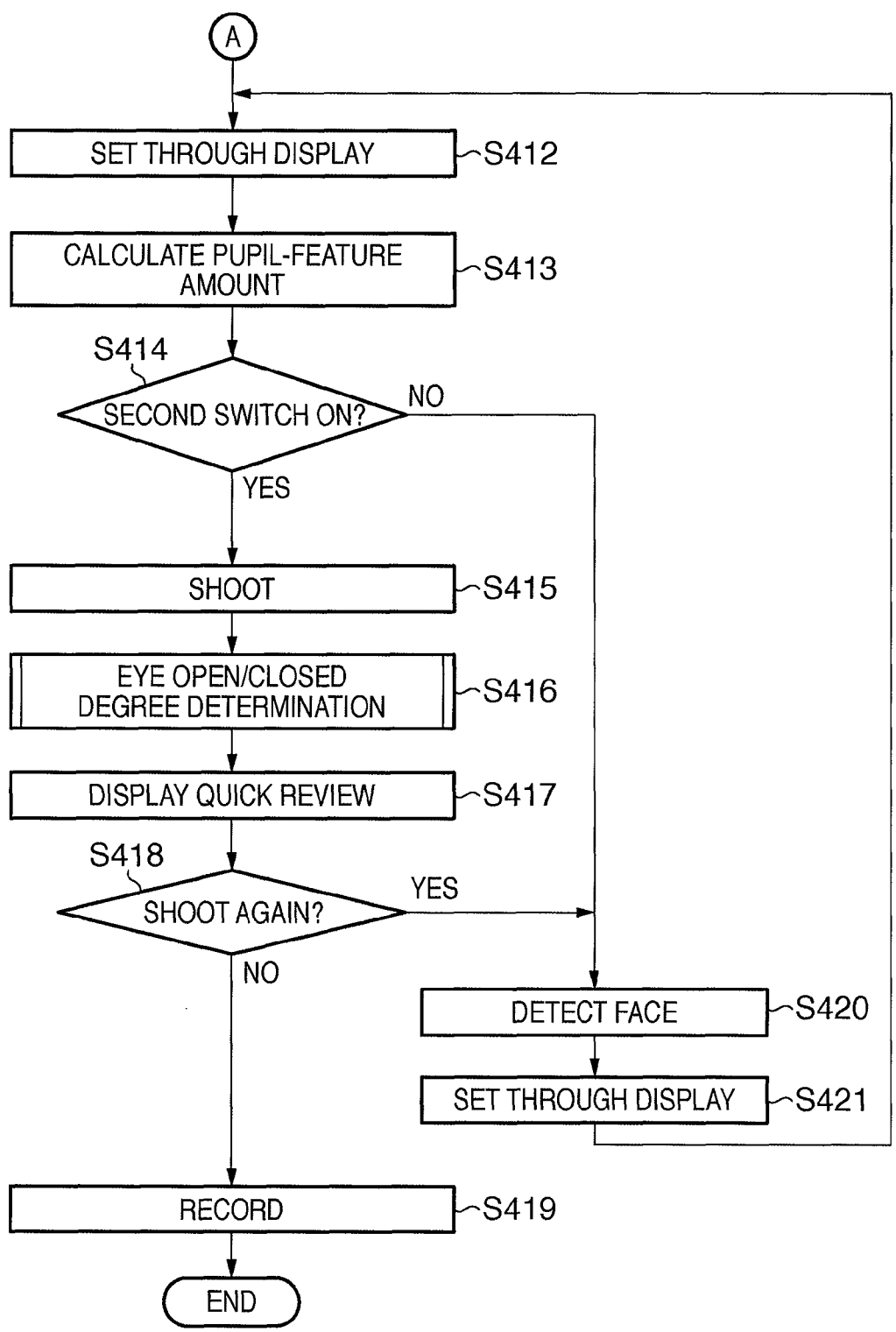

FIGS. 14A and 14B show an example of a processing sequence in an image sensing apparatus 100 according to the third embodiment. Processes in step S400 to S408 are the same as those in steps S100 to S108 in FIG. 2A in the first embodiment, and a description thereof will be omitted.

If the user presses the first switch (focusing switch) in step S409 (YES in step S409), face detection, AE/AF control, and through display processing are executed similarly to the first embodiment (steps S410 to S412). After the through display, the pupil-feature amount is calculated for a predetermined time (step S413). More specifically, by the same method as that in the second embodiment, the pupil-feature amount is calculated from frame images sequentially input within a predetermined time (time $t=t_2[s]$ to time $t=t_{n2}[s]$).

If the user presses the second switch (shooting switch) (YES in step S414), shooting is done (step S415). In this case, shooting is performed regardless of the eye open/closed state. At this time, a sensed image is temporarily stored in a memory 108 shown in FIG. 1. In addition to the sensed high-resolution image, the memory 108 also stores a low-resolution image compressed for use in eye open/closed determination.

If the user does not press the second switch in step S414 (NO in step S414), face detection (step S420) and through display (step S421) are executed again. Then, the process returns to step S413.

If shooting is done in step S415, a system control circuit 112 performs eye open/closed determination using the compressed low-resolution image (step S416). Details of the eye open/closed degree determination will be explained later.

The system control circuit 112 displays a quick review on the image sensing apparatus 100 (step S417). At this time, if it is determined in the eye open/closed degree determination that the eyes are closed, a message such as "would you like to shoot again?" is displayed to prompt the user to shoot again. It is also possible to force the user to shoot without any display which prompts him to shoot again.

If the user does not want to shoot again (NO in step S418), the system control circuit 112 records, in a flash memory or the like, the high-resolution sensed image stored in the memory 108 (step S419). Then, the process ends. If the user wants to shoot again (YES in step S418), the system control circuit 112 performs face detection for the next frame image (step S420), and a through display (step S421). After that, the process returns to step S413.

Figure 15:
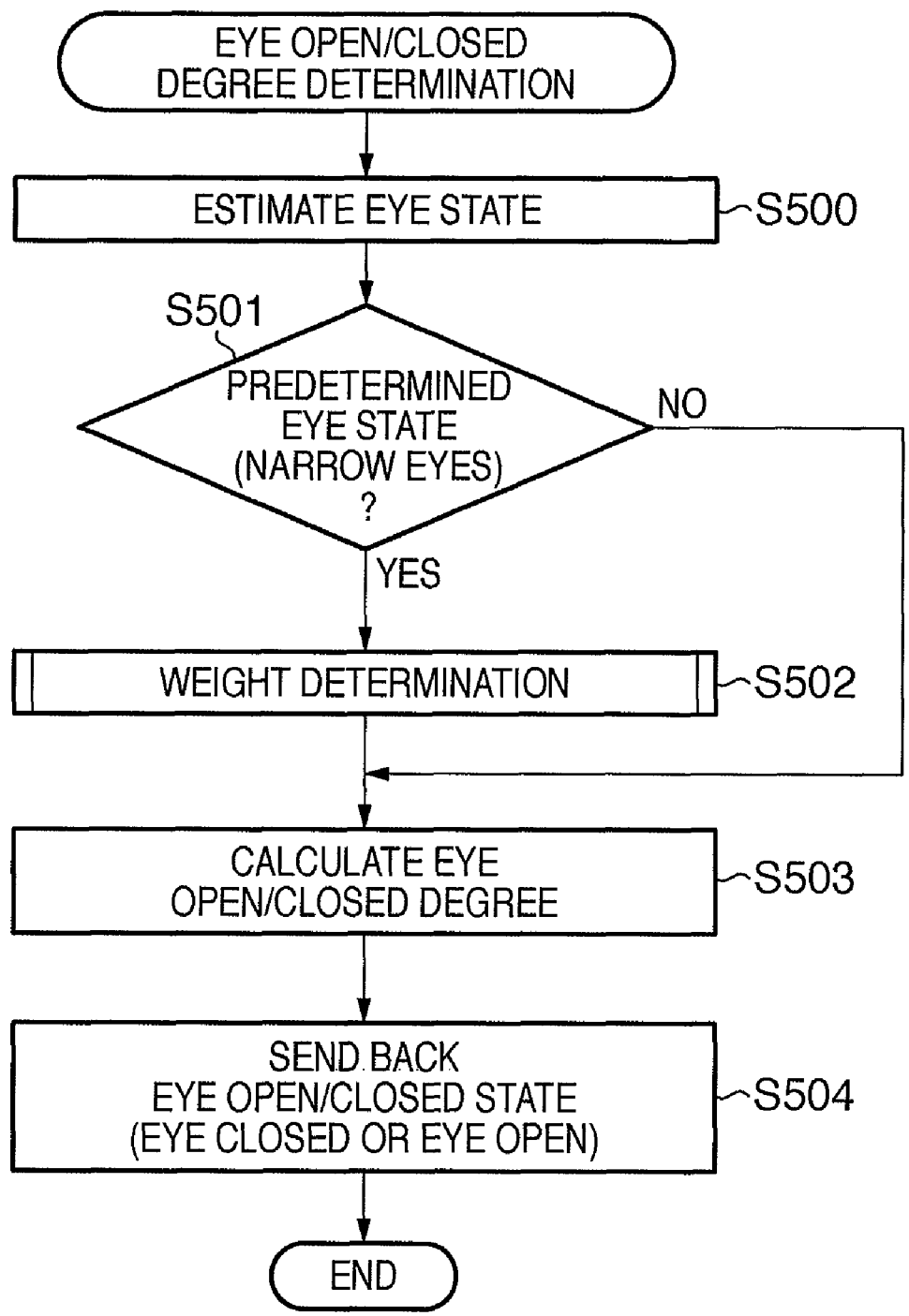
FIG. 15 is a flowchart showing an example of the sequence of eye open/closed degree determination in step S416 shown in FIG. 14B.

Details of the eye open/closed degree determination in step S416 shown in FIG. 14B will be explained with reference to a FIG. 15. In the third embodiment, to prevent a repetitive description, a description of detailed processing (e.g., methods of detecting and calculating a pupil-feature amount) described in the first and second embodiments will be omitted, and only a rough sequence representing the difference will be explained.

When this processing starts, the system control circuit 112 refers to pupil-feature amounts Feature1($t_2$), ..., Feature1 ($t_{n2}$) calculated in step S413 (FIG. 14B) from time $t=t_2[s]$ to time $t=t_{n2}[s]$. The system control circuit 112 estimates a state in which the eyes of a face detected in step S410 (FIG. 14A) or step S420 (FIG. 14B) are open (step S500). Similar to the second embodiment, whether the eyes are in a predetermined eye state is determined by comparing, with a predetermined threshold $L_{th}$, the width L between the maximum and minimum values of the pupil-feature amount Feature1(t) within a predetermined time. Note that the pupil-feature amounts Feature1($t_2$), ..., Feature1($t_{n2}$) from time $t=t_2[s]$ to time $t=t_{n2}[s]$ are stored in the memory 108 in FIG. 1, as described above.

If the system control circuit 112 determines that the eyes are in the predetermined eye state, that is, are narrow (YES in step S501), it executes weight determination (step S502). Details of the weight determination will be described later. After the weight determination, the system control circuit 112 performs processing such as weighting similarly to the first embodiment, and then calculates a final eye open/closed degree BlinkDegree($t_{n2}$) (step S503). That is, the system control circuit 112 calculates the eye open/closed degree using both the pupil-feature amount and feature-change amount.

If the eyes are not in the predetermined eye state, that is, are not narrow (NO in step S501), the system control circuit 112 performs processing such as weighting similarly to the first embodiment, and then calculates the final eye open/closed degree BlinkDegree($t_{n2}$) (step S503). Also in this case, the system control circuit 112 calculates the eye open/closed degree using both the pupil-feature amount and feature-change amount.

Thereafter, the system control circuit 112 determines the eye open/closed state by executing threshold processing for the calculated eye open/closed degree BlinkDegree($t_{n2}$), and sends back the determination result (eye closed or eye open) (step S504). Then, the process ends.

Figure 16:
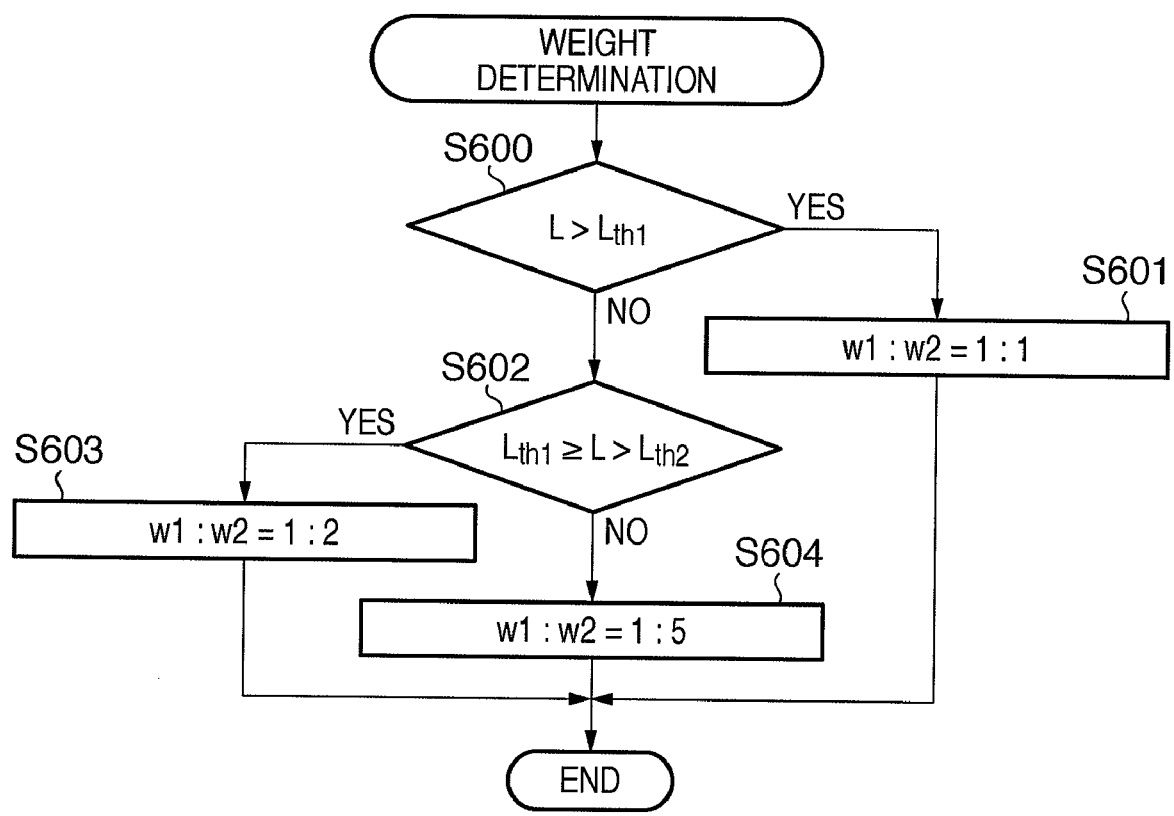
FIG. 16 is a flowchart showing an example of the sequence of weight determination in step S502 shown in FIG. 15.
Figure 19:
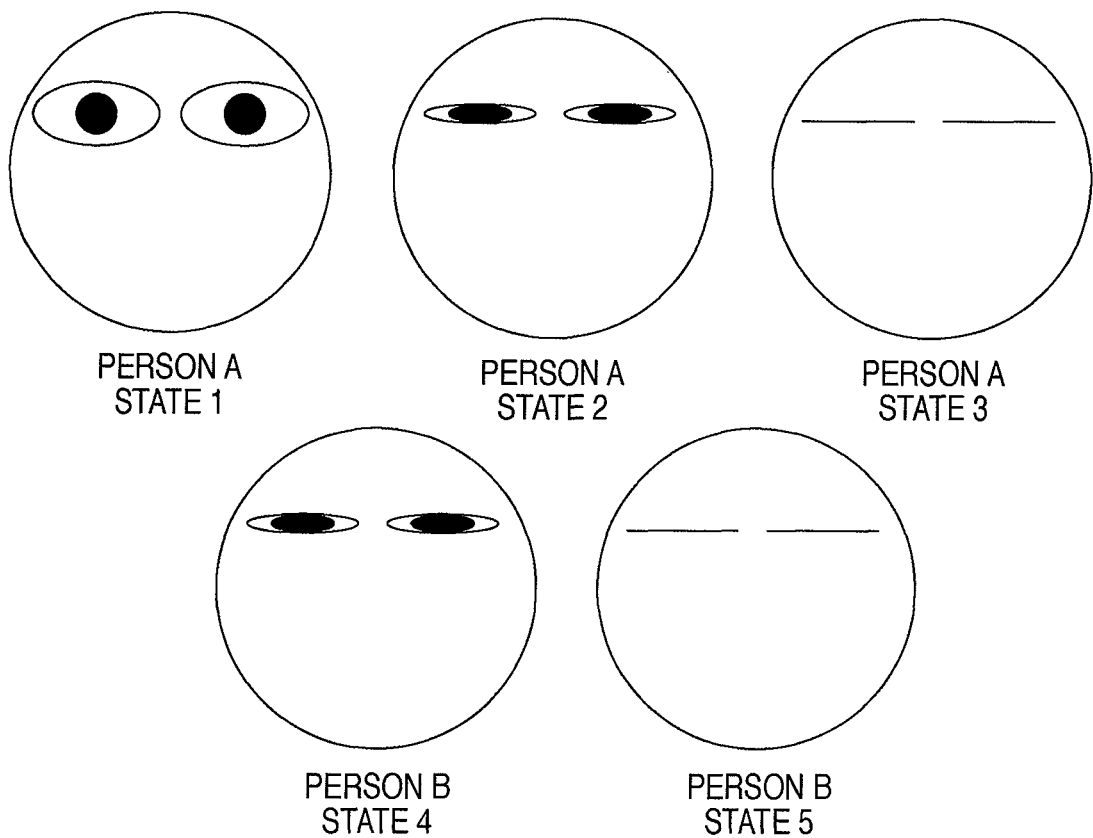
FIG. 19 is a first view for explaining a conventional problem.

Details of the weight determination in step S502 shown in FIG. 15 will be explained with reference to FIG. 16. In the following description, thresholds which satisfy a relation "$L_{th1}>L_{th2}$" are used to determine weights. Note that the weights are determined using a table prepared in advance.

When this processing starts, the system control circuit 112 determines whether the width L of the pupil-feature amount Feature1(t) calculated within a predetermined time in step S413 (FIG. 14B) satisfies $L>L_{th1}$. If $L>L_{th1}$ (YES in step S600), the weights $w_1$ and $w_2$ are determined to be 1:1 (step S601), and then the process ends.

If $L<L_{th1}$ (NO in step S600), the system control circuit 112 determines whether $L_{th1} \geqq L>L_{th2}$ holds. If $L_{th1}>L>L_{th2}$ (YES in step S602), the weights $w_1$ and $w_2$ are determined to be 1:2 (step S603), and then the process ends. If $L<L_{th2}$ (NO in step S602), the weights $w_1$ and $w_2$ are determined to be 1:5 (step S604), and then the process ends. That is, as the width L between the maximum and minimum values of the pupil-feature amount Feature1(t) within a predetermined time becomes smaller, the weight $w_2$ of the eye open/closed degree BlinkDegree2($t_{n2}$) is set larger.

The processes described with reference to FIGS. 15 and 16 change the set weights only when the eyes correspond to a predetermined eye state (narrow eyes), but the present invention is not limited to this. For example, when the eyes of a person are not in a predetermined eye state, for example, are large, the weight $w_1$ may also be set larger than the weight $w_2$.

FIGS. 17 and 18 are views for explaining effects obtained by setting the weight $w_2$ of the eye open/closed degree BlinkDegree2($t_{n2}$) calculated based on the feature-change amount Feature2($t_{n2}$) upon detecting a predetermined eye state.

For person A whose eyes are not in a predetermined eye state, that is, are not narrow, as shown in FIG. 17, the weight $w_1$ of BlinkDegree1($t_{n2}$) and the weight $w_2$ of the eye open/closed degree BlinkDegree2($t_{n2}$) are set to 1:1.

In contrast, for a person whose eyes are in a predetermined eye state, that is, are narrow, like person B shown in FIG. 17, the weight $w_1$ of BlinkDegree1($t_{n2}$) and the weight $w_2$ of the eye open/closed degree BlinkDegree2($t_{n2}$) are set to 1:2. That is, the weight $w_2$ is set larger. With this setting, state 2 of person A and state 4' of person B can be distinguished from each other. Further, state 3 of person A whose eyes are not narrow and state 5 of person B whose eyes are narrow can be determined to have the same eye open/closed degree.

For a person whose eyes are very narrow, like person B shown in FIG. 18, the weight $w_2$ of the eye open/closed degree BlinkDegree2($t_{n2}$) calculated based on the feature-change amount Feature2($t_{n2}$) is set much larger. With this setting, the eye open/closed degree can be determined regardless of individual differences in eye size.

As described above, according to the third embodiment, it is determined from a change of the pupil-feature amount within a predetermined time whether the eye size of a person to undergo determination of the eye open/closed state is in a predetermined eye state (narrow eyes). Weights are changed based on the determination result, and then the eye open/closed degree is determined. As a result, an eye state can be detected at higher precision regardless of eye size.

Typical embodiments of the present invention have been described above. However, the present invention is not limited to the above-described embodiments and embodiments shown in the accompanying drawings, and can be properly modified without departing from the scope of the appended claims.

For example, in the second and third embodiments, a state in which the eyes are narrow is determined as a predetermined eye state. However, the present invention is not limited to this, and a state in which the eyes are large may also be determined as a predetermined eye state. Also in this case, the same processing as that described above can be adopted.

In the second and third embodiments, a predetermined eye state is estimated by comparing, with the predetermined threshold $L_{th}$, the width L between the maximum and minimum values of the pupil-feature amount Feature1(t) within a predetermined time. However, the present invention is not limited to this. For example, a predetermined eye state may also be estimated by comparing, with a predetermined threshold, the average value of the pupil-feature amount Feature1(t) within a predetermined time.

Some or all processes described in the first to third embodiments may also be combined. For example, the processing described in the second embodiment to switch the method of determining the eye open/closed degree, and the weight determination described in the third embodiment may also be executed in combination.

The present invention also includes a case where the functions of the above-described embodiments are achieved by supplying a software program to a system or apparatus directly or from a remote place, and reading out and executing the supplied program codes by a computer incorporated in the system or apparatus. In this case, the supplied program is a computer program corresponding to the flowcharts shown in the drawings in the embodiments.

Hence, the program codes installed in the computer to implement functional processing of the present invention by the computer also implement the present invention. That is, the present invention also includes the computer program for implementing functional processing of the present invention. In this case, the program may take the form of an object code, a program executed by an interpreter, or script data supplied to an OS (Operating System) as long as the functions of the program can be provided.

Various types of the computer-readable storage media may be used for supplying the computer program.

The program can also be supplied by downloading the computer program of the present invention from an Internet homepage to a storage medium such as a hard disk. The program can also be supplied by grouping program codes which form the program of the present invention into a plurality of files, and downloading the files from different homepages.

Further, the functions of the above-described embodiments are also implemented in cooperation with the OS or the like running on the computer on the basis of the instructions of the program.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2008-051121 filed on Feb. 29, 2008, which is hereby incorporated by reference herein in its entirety.

What is claimed is:

1. An information processing apparatus comprising:
an input unit configured to input an image;
a face detection unit configured to detect a face of a person from the image input from said input unit;
a first calculation unit configured to calculate a feature amount associated with an eye open/closed state from the face detected by said face detection unit;
a second calculation unit configured to calculate, as a feature-change amount, a difference between the feature amount calculated by said first calculation unit and a feature amount calculated from a face detected from an image input before a predetermined time;
a third calculation unit configured to calculate an eye open/closed degree of eyes of the face detected by said face detection unit on the basis of the feature amount and the feature-change amount; and
a weighting unit configured to set weights for the feature amount calculated by said first calculation unit and the feature-change amount calculated by said second calculation unit,
wherein said third calculation unit calculates the eye open/closed degree of eyes of the face detected by said face detection unit on the basis of the feature amount and the feature-change amount for which said weighting unit sets the weights
wherein said first calculation unit calculates a feature amount associated with an eye open/closed state of a person from faces of the person that are detected from a plurality of images input from said input unit within a predetermined time, and
wherein said third calculation unit calculates the eye open/closed degree of eyes of the face detected by said face detection unit on the basis of only the weighted feature amount when a difference between a maximum value and a minimum value in a plurality of feature amounts calculated by said first calculation unit from the plurality of images has a predetermined relation with a preset threshold.

2. The apparatus according to claim 1, further comprising a determination unit configured to perform eye open/closed determination by performing threshold processing for the eye open/closed degree calculated by said third calculation unit.

3. An information processing apparatus comprising:
an input unit configured to input an image;
a face detection unit configured to detect a face of a person from the image input from said input unit;
a first calculation unit configured to calculate a feature amount associated with an eye open/closed state from the face detected by said face detection unit;
a second calculation unit configured to calculate, as a feature-change amount, a difference between the feature amount calculated by said first calculation unit and a feature amount calculated from a face detected from an image input before a predetermined time;
a third calculation unit configured to calculate an eye open/closed degree of eyes of the face detected by said face detection unit on the basis of the feature amount and the feature-change amount; and
a weighting unit configured to set weights for the feature amount calculated by said first calculation unit and the feature-change amount calculated by said second calculation unit,
wherein said third calculation unit calculates the eye open/closed degree of eyes of the face detected by said face detection unit on the basis of the feature amount and the feature-change amount for which said weighting unit sets the weights
wherein said first calculation unit calculates a feature amount associated with an eye open/closed state of a person from faces of the person that are detected from a plurality of images input from said input unit within a predetermined time,
wherein said weighting unit changes the weights set for the feature amount and the feature-change amount on the basis of a plurality of feature amounts calculated by said first calculation unit from the plurality of images wherein said first calculation unit calculates a pupil-feature amount as the feature amount associated with the eye open/closed state, and wherein said weighting unit sets the weight for the feature-change amount to be larger than the weight set for the feature amount when a difference between a maximum value and a minimum value in a plurality of feature amounts calculated by said first calculation unit from the plurality of images is smaller than a predetermined threshold.

4. An information processing apparatus comprising:

an input unit configured to input an image;

a face detection unit configured to detect a face of a person from the image input from said input unit;

a first calculation unit configured to calculate a feature amount associated with an eye open/closed state from the face detected by said face detection unit;

a second calculation unit configured to calculate, as a feature-change amount, a difference between the feature amount calculated by said first calculation unit and a feature amount calculated from a face detected from an image input before a predetermined time;

a third calculation unit configured to calculate an eye open/closed degree of eyes of the face detected by said face detection unit on the basis of the feature amount and the feature-change amount; and a weighting unit configured to set weights for the feature amount calculated by said first calculation unit and the feature-change amount calculated by said second calculation unit, wherein said third calculation unit calculates the eye open/closed degree of eyes of the face detected by said face detection unit on the basis of the feature amount and the feature-change amount for which said weighting unit sets the weights, wherein said first calculation unit calculates a feature amount associated with an eye open/closed state of a person from faces of the person that are detected from a plurality of images input from said input unit within a predetermined time, wherein said weighting unit changes the weights set for the feature amount and the feature-change amount on the basis of a plurality of feature amounts calculated by said first calculation unit from the plurality of images wherein said first calculation unit calculates a pupil-feature amount as the feature amount associated with the eye open/closed state, and wherein said weighting unit sets the weight for the feature amount to be larger than the weight set for the feature-change amount when a difference between a maximum value and a minimum value in a plurality of feature amounts calculated by said first calculation unit from the plurality of images is larger than a predetermined threshold.

5. An eye open/closed degree determination method comprising:

inputting an image;

detecting a face of a person from the image input in the inputting the image;

calculating a feature amount associated with an eye open/closed state from the face detected in the detecting the face;

calculating, as a feature-change amount, a difference between the feature amount calculated in the calculating the feature amount and a feature amount calculated from a face detected from an image input before a predetermined time;

calculating an eye opening/closing degree of eyes of the face detected in the detecting the face on the basis of the feature amount and the feature-change amount; and setting weights for the feature amount calculated by said first calculation step and the feature-change amount calculated by said second calculation step, wherein said third calculation step calculates the eye open/closed degree of eyes of the face detected by said face detection step on the basis of the feature amount and the feature-change amount for which said weighting step sets the weights, wherein said first calculation step calculates a feature amount associated with an eye open/closed state of a person from faces of the person that are detected from a plurality of images input from said input step within a predetermined time, and wherein said third calculation step calculates the eye open/closed degree of eyes of the face detected by said face detection step on the basis of only the weighted feature amount when a difference between a maximum value and a minimum value in a plurality of feature amounts calculated by said first calculation step from the plurality of images has a predetermined relation with a preset threshold.

6. A non-transitory computer-readable storage medium storing a computer program, the program causing a computer to function as an input unit configured to input an image, a face detection unit configured to detect a face of a person from the image input from said input unit, a first calculation unit configured to calculate a feature amount associated with an eye open/closed state from the face detected by said face detection unit, a second calculation unit configured to calculate, as a feature-change amount, a difference between the feature amount calculated by said first calculation unit and a feature amount calculated from a face detected from an image input before a predetermined time, and a third calculation unit configured to calculate an eye open/closed degree of eyes of the face detected by said face detection unit on the basis of the feature amount and the feature-change amount; and a weighting unit for setting weights for the feature amount calculated by said first calculation unit and the feature-change amount calculated by said second calculation unit, wherein said third calculation unit calculates the eye open/closed degree of eyes of the face detected by said face detection unit on the basis of the feature amount and the feature-change amount for which said weighting unit sets the weights, wherein said first calculation unit calculates a feature amount associated with an eye open/closed state of a person from faces of the person that are detected from a plurality of images input from said input unit within a predetermined time, and wherein said third calculation unit calculates the eye open/closed degree of eyes of the face detected by said face detection unit on the basis of only the weighted feature amount when a difference between a maximum value and a minimum value in a plurality of feature amounts calculated by said first calculation unit from the plurality of images has a predetermined relation with a preset threshold.

7. An image sensing apparatus comprising:
an input unit configured to input an image;
a face detection unit configured to detect a face of a person from the image input from said input unit;
a first calculation unit configured to calculate a feature amount associated with an eye open/closed state from the face detected by said face detection unit;
a second calculation unit configured to calculate, as a feature-change amount, a difference between the feature amount calculated by said first calculation unit and a feature amount calculated from a face detected from an image input before a predetermined time;
a third calculation unit configured to calculate an eye open/closed degree of eyes of the face detected by said face detection unit on the basis of the feature amount and the feature-change amount;
a determination unit configured to perform eye open/closed determination by performing threshold processing for the eye open/closed degree calculated by said third calculation unit; and
an image sensing unit configured to shoot on the basis of a result of eye open/closed degree determination by said determination unit; and
a weighting unit for setting weights for the feature amount calculated by said first calculation unit and the feature-change amount calculated by said second calculation unit,
wherein said third calculation unit calculates the eye open/closed degree of eyes of the face detected by said face detection unit on the basis of the feature amount and the feature-change amount for which said weighting unit sets the weights,
wherein said first calculation unit calculates a feature amount associated with an eye open/closed state of a person from faces of the person that are detected from a plurality of images input from said input unit within a predetermined time, and
wherein said third calculation unit calculates the eye open/closed degree of eyes of the face detected by said face detection unit on the basis of only the weighted feature amount when a difference between a maximum value and a minimum value in a plurality of feature amounts calculated by said first calculation unit from the plurality of images has a predetermined relation with a preset threshold.

8. An eye open/closed degree determination method comprising:
an input step configured to input an image;
a face detection step configured to detect a face of a person from the image input from said input step;
a first calculation step configured to calculate a feature amount associated with an eye open/closed state from the face detected by said face detection step;
a second calculation step configured to calculate, as a feature-change amount, a difference between the feature amount calculated by said first calculation step and a feature amount calculated from a face detected from an image input before a predetermined time;
a third calculation step configured to calculate an eye open/closed degree of eyes of the face detected by said face detection step on the basis of the feature amount and the feature-change amount; and a weighting step configured to set weights for the feature amount calculated by said first calculation step and the feature-change amount calculated by said second calculation step,
wherein said third calculation step calculates the eye open/closed degree of eyes of the face detected by said face detection step on the basis of the feature amount and the feature-change amount for which said weighting step sets the weights,
wherein said first calculation step calculates a feature amount associated with an eye open/closed state of a person from faces of the person that are detected from a plurality of images input from said input step within a predetermined time,
wherein said weighting step changes the weights set for the feature amount and the feature-change amount on the basis of a plurality of feature amounts calculated by said first calculation step from the plurality of images,
wherein said first calculation step calculates a pupil-feature amount as the feature amount associated with the eye open/closed state, and
wherein said weighting step sets the weight for the feature-change amount to be larger than the weight set for the feature amount when a difference between a maximum value and a minimum value in a plurality of feature amounts calculated by said first calculation step from the plurality of images is smaller than a predetermined threshold.

9. A non-transitory computer-readable storage medium storing a computer program, the program causing a computer to function as:
an input unit configured to input an image;
a face detection unit configured to detect a face of a person from the image input from said input unit;
a first calculation unit configured to calculate a feature amount associated with an eye open/closed state from the face detected by said face detection unit;
a second calculation unit configured to calculate, as a feature-change amount, a difference between the feature amount calculated by said first calculation unit and a feature amount calculated from a face detected from an image input before a predetermined time;
a third calculation unit configured to calculate an eye open/closed degree of eyes of the face detected by said face detection unit on the basis of the feature amount and the feature-change amount; and
a weighting unit configured to set weights for the feature amount calculated by said first calculation unit and the feature-change amount calculated by said second calculation unit,
wherein said third calculation unit calculates the eye open/closed degree of eyes of the face detected by said face detection unit on the basis of the feature amount and the feature-change amount for which said weighting unit sets the weights
wherein said first calculation unit calculates a feature amount associated with an eye open/closed state of a person from faces of the person that are detected from a plurality of images input from said input unit within a predetermined time,
wherein said weighting unit changes the weights set for the feature amount and the feature-change amount on the basis of a plurality of feature amounts calculated by said first calculation unit from the plurality of images,
wherein said first calculation unit calculates a pupil-feature amount as the feature amount associated with the eye open/closed state, and wherein said weighting unit sets the weight for the feature-change amount to be larger than the weight set for the feature amount when a difference between a maximum value and a minimum value in a plurality of feature amounts calculated by said first calculation unit from the plurality of images is smaller than a predetermined threshold.

10. An image sensing apparatus comprising:
an input unit configured to input an image;
a face detection unit configured to detect a face of a person from the image input from said input unit;
a first calculation unit configured to calculate a feature amount associated with an eye open/closed state from the face detected by said face detection unit;
a second calculation unit configured to calculate, as a feature-change amount, a difference between the feature amount calculated by said first calculation unit and a feature amount calculated from a face detected from an image input before a predetermined time;
a third calculation unit configured to calculate an eye open/closed degree of eyes of the face detected by said face detection unit on the basis of the feature amount and the feature-change amount; and
a weighting unit configured to set weights for the feature amount calculated by said first calculation unit and the feature-change amount calculated by said second calculation unit,
wherein said third calculation unit calculates the eye open/closed degree of eyes of the face detected by said face detection unit on the basis of the feature amount and the feature-change amount for which said weighting unit sets the weights,
wherein said first calculation unit calculates a feature amount associated with an eye open/closed state of a person from faces of the person that are detected from a plurality of images input from said input unit within a predetermined time,
wherein said weighting unit changes the weights set for the feature amount and the feature-change amount on the basis of a plurality of feature amounts calculated by said first calculation unit from the plurality of images,
wherein said first calculation unit calculates a pupil-feature amount as the feature amount associated with the eye open/closed state, and
wherein said weighting unit sets the weight for the feature-change amount to be larger than the weight set for the feature amount when a difference between a maximum value and a minimum value in a plurality of feature amounts calculated by said first calculation unit from the plurality of images is smaller than a predetermined threshold.

11. An eye open/closed degree determination method comprising:
an input step configured to input an image;
a face detection step configured to detect a face of a person from the image input from said input step;
a first calculation step configured to calculate a feature amount associated with an eye open/closed state from the face detected by said face detection step;
a second calculation step configured to calculate, as a feature-change amount, a difference between the feature amount calculated by said first calculation step and a feature amount calculated from a face detected from an image input before a predetermined time;
a third calculation step configured to calculate an eye open/closed degree of eyes of the face detected by said face detection step on the basis of the feature amount and the feature-change amount; and
a weighting step configured to set weights for the feature amount calculated by said first calculation step and the feature-change amount calculated by said second calculation step,
wherein said third calculation step calculates the eye open/closed degree of eyes of the face detected by said face detection step on the basis of the feature amount and the feature-change amount for which said weighting step sets the weights,
wherein said first calculation step calculates a feature amount associated with an eye open/closed state of a person from faces of the person that are detected from a plurality of images input from said input step within a predetermined time,
wherein said weighting step changes the weights set for the feature amount and the feature-change amount on the basis of a plurality of feature amounts calculated by said first calculation step from the plurality of images,
wherein said first calculation step calculates a pupil-feature amount as the feature amount associated with the eye open/closed state, and
wherein said weighting step sets the weight for the feature amount to be larger than the weight set for the feature-change amount when a difference between a maximum value and a minimum value in a plurality of feature amounts calculated by said first calculation step from the plurality of images is larger than a predetermined threshold.

12. A non-transitory computer-readable storage medium storing a computer program, the program causing a computer to function as:
an input unit configured to input an image;
a face detection unit configured to detect a face of a person from the image input from said input unit;
a first calculation unit configured to calculate a feature amount associated with an eye open/closed state from the face detected by said face detection unit;
a second calculation unit configured to calculate, as a feature-change amount, a difference between the feature amount calculated by said first calculation unit and a feature amount calculated from a face detected from an image input before a predetermined time;
a third calculation unit configured to calculate an eye open/closed degree of eyes of the face detected by said face detection unit on the basis of the feature amount and the feature-change amount; and
a weighting unit configured to set weights for the feature amount calculated by said first calculation unit and the feature-change amount calculated by said second calculation unit,
wherein said third calculation unit calculates the eye open/closed degree of eyes of the face detected by said face detection unit on the basis of the feature amount and the feature-change amount for which said weighting unit sets the weights,
wherein said first calculation unit calculates a feature amount associated with an eye open/closed state of a person from faces of the person that are detected from a plurality of images input from said input unit within a predetermined time, and
wherein said weighting unit changes the weights set for the feature amount and the feature-change amount on the basis of a plurality of feature amounts calculated by said first calculation unit from the plurality of images, wherein said first calculation unit calculates a pupil-feature amount as the feature amount associated with the eye open/closed state, and wherein said weighting unit sets the weight for the feature amount to be larger than the weight set for the feature-change amount when a difference between a maximum value and a minimum value in a plurality of feature amounts calculated by said first calculation unit from the plurality of images is larger than a predetermined threshold.

13. An image sensing apparatus comprising:

an input unit configured to input an image;

a face detection unit configured to detect a face of a person from the image input from said input unit;

a first calculation unit configured to calculate a feature amount associated with an eye open/closed state from the face detected by said face detection unit;

a second calculation unit configured to calculate, as a feature-change amount, a difference between the feature amount calculated by said first calculation unit and a feature amount calculated from a face detected from an image input before a predetermined time;

a third calculation unit configured to calculate an eye open/closed degree of eyes of the face detected by said face detection unit on the basis of the feature amount and the feature-change amount; and a weighting unit configured to set weights for the feature amount calculated by said first calculation unit and the feature-change amount calculated by said second calculation unit, wherein said third calculation unit calculates the eye open/closed degree of eyes of the face detected by said face detection unit on the basis of the feature amount and the feature-change amount for which said weighting unit sets the weights wherein said first calculation unit calculates a feature amount associated with an eye open/closed state of a person from faces of the person that are detected from a plurality of images input from said input unit within a predetermined time, wherein said weighting unit changes the weights set for the feature amount and the feature-change amount on the basis of a plurality of feature amounts calculated by said first calculation unit from the plurality of images, wherein said first calculation unit calculates a pupil-feature amount as the feature amount associated with the eye open/closed state, and wherein said weighting unit sets the weight for the feature amount to be larger than the weight set for the feature-change amount when a difference between a maximum value and a minimum value in a plurality of feature amounts calculated by said first calculation unit from the plurality of images is larger than a predetermined threshold.

* * * * *